(12) United States Patent
Krishnan et al.

(10) Patent No.: US 8,815,555 B2
(45) Date of Patent: *Aug. 26, 2014

(54) NUCLEIC ACID SAMPLE PREPARATION

(71) Applicant: Biological Dynamics, Inc., San Diego, CA (US)

(72) Inventors: Rajaram Krishnan, San Diego, CA (US); David Charlot, San Diego, CA (US); Eugene Tu, San Diego, CA (US); James McCanna, San Diego, CA (US); Lucas Kumosa, Centennial, CO (US); Paul Swanson, Santee, CA (US); Robert Turner, San Diego, CA (US); Kai Yang, San Diego, CA (US); Irina Dobrovolskaya, San Diego, CA (US); David Liu, San Diego, CA (US)

(73) Assignee: Biological Dynamics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/201,726

(22) Filed: Mar. 7, 2014

(65) Prior Publication Data

US 2014/0183043 A1 Jul. 3, 2014

Related U.S. Application Data

(63) Continuation of application No. 14/067,841, filed on Oct. 30, 2013, which is a continuation of application No. 13/864,179, filed on Apr. 16, 2013, now Pat. No. 8,603,791.

(60) Provisional application No. 61/624,897, filed on Apr. 16, 2012.

(51) Int. Cl.
*C12N 13/00* (2006.01)
*G01N 27/447* (2006.01)

(52) U.S. Cl.
CPC .............. *G01N 27/44704* (2013.01)
USPC ................... 435/173.1; 435/173.9

(58) Field of Classification Search
CPC ...... C12N 1/02; C12N 15/10; C12N 15/1003; C12N 13/00; C12N 15/101
See application file for complete search history.

(56) References Cited

U.S. PATENT DOCUMENTS

| | | | |
|---|---|---|---|
| 5,632,957 A | 5/1997 | Heller et al. | |
| 6,280,590 B1 | 8/2001 | Cheng et al. | |
| 6,403,367 B1 | 6/2002 | Cheng et al. | |
| 6,749,736 B1 | 6/2004 | Fuhr et al. | |
| 6,824,664 B1 | 11/2004 | Austin et al. | |
| 7,105,081 B2 | 9/2006 | Gascoyne et al. | |
| 8,603,791 B2 | 12/2013 | Krishnan et al. | |
| 2001/0045359 A1 | 11/2001 | Cheng et al. | |
| 2003/0146100 A1 | 8/2003 | Huang et al. | |
| 2006/0063183 A1 | 3/2006 | Segawa et al. | |
| 2006/0289341 A1 | 12/2006 | Muller et al. | |
| 2007/0095669 A1 | 5/2007 | Lau et al. | |
| 2007/0125650 A1 | 6/2007 | Scurati et al. | |
| 2007/0131554 A1 | 6/2007 | Yu et al. | |
| 2007/0240495 A1 | 10/2007 | Hirahara | |
| 2007/0284254 A1 | 12/2007 | Cho et al. | |
| 2011/0108422 A1 | 5/2011 | Heller et al. | |
| 2013/0273640 A1 | 10/2013 | Krishnan et al. | |
| 2014/0048417 A1 | 2/2014 | Heller et al. | |
| 2014/0127697 A1 | 5/2014 | Krishnan et al. | |
| 2014/0174931 A1 | 6/2014 | Krishnan et al. | |
| 2014/0183042 A1 | 7/2014 | Krishnan et al. | |

FOREIGN PATENT DOCUMENTS

| | | |
|---|---|---|
| EP | 1775589 | 4/2007 |
| JP | 2002-502047 | 1/2002 |
| JP | 2004-532968 | 10/2004 |
| JP | 2001-500252 | 1/2009 |
| WO | WO99/38612 | 8/1999 |
| WO | WO01/96025 | 12/2001 |
| WO | WO2005/121767 | 12/2005 |
| WO | WO2006/018981 | 2/2006 |
| WO | WO-2007-107910 | 9/2007 |
| WO | WO 2009-146143 | 12/2009 |

OTHER PUBLICATIONS

Asbury, C.L; Diercks, A.H.; Van Den Engh, G. Trapping of DNA by dielectrophoresis. Electrophoresis. 23:2658-2666; 2002.
Asbury, C.L; Van Den Engh, G. Trapping of DNA in Nonuniform Oscillating Electric Fields. Biophys J. 74:1024-1030; 1998.
Becker, F.F.; Wang, X-B.; Huang, Y.; Pethig, R.; Vykoukalt, Y.; Gascoyne, P.R.C. Separation of Human Breast Cancer Cells From Blood by Differential Dielectric Affinity. Proceedings of the National Academy of Sciences, 92:860-864; 1995.
Becker, F.F.; Wang, X-B.; Huang, Y.; Pethig, R.; Vykoukalt, Y.; Gascoyne, P.R.C. The removal of human leukemia cells from blood using interdigitated microelectrodes. J Phys. D: Appl. Phys. 27:2659-2662; 1994.
Board et al, "DNA Methylation in Circulating Tumour DNA as a Biomarker for Cancer", Biomark Insights, 2:307-19 (2007).
Cheng, J. et al., "Preparation and Hybridization Analysis of DNA/A from *E. coli* on 15 Microfabricated Bioelectronic Chips", Nature Biotechnology, vol. 16, pp. 541-546, 1998.
Ching et al., "Isolation of Cultured Cerivcal Carcinoma Cells Mixed with Peripheral Blood Cells on a Bioelectronic Chip", Analytical Chemistry, vol. 70, #11, pp. 2321-2326, 1998.
CN200980118202.3 Office Action dated Dec. 21, 2012.
EP 09755505.6 Extended Search Report dated Jun. 18, 2012.
EP Application No. 09755505.6 Communication pursuant to Rules 70(2) and 70a(2) EPC in dated Jul. 5, 2012.

(Continued)

*Primary Examiner* — James Martinell
(74) *Attorney, Agent, or Firm* — Wilson Sonsini Goodrich & Rosati

(57) ABSTRACT

The present invention includes methods, devices and systems for isolating a nucleic acid from a fluid comprising cells. In various aspects, the methods, devices and systems may allow for a rapid procedure that requires a minimal amount of material and/or results in high purity nucleic acid isolated from complex fluids such as blood or environmental samples.

21 Claims, 10 Drawing Sheets

(56) References Cited

OTHER PUBLICATIONS

Gautschi et al, "Circulating deoxyribonucleic Acid as prognostic marker in non-small-cell lung cancer patients undergoing chemotherapy." J Clin Oncol., 22(20):4157-64 (2004).
GB1007402.9 Exam Report dated Nov. 2, 2010.
Goodard W.A., Brenner, D.W.; Lyshevski, S.B.; Iafrate, G.J.; Handbook of Nanoscience, $2^{nd}$ edition, 2007, Ch 16, p. 5-8.
Green, N. G.; Ramos, A.; Morgan, H. Ac electrokinetics: a survey of sub-micrometre particle dynamics. J. Phys. D: Appl. Phys. 33:632-641; 2000.
Higuchi Y., Chromosomal DNA fragmentation in apoptosis and necrosis induced by oxidative stress. Biochem Pharacol. 66:1527-35. 2003.
Higuchi Y.; Matsukawa S. Appearance of 1-2 Mbp giant DNA fragments as an early common response leading to cell death induced by various substances that cause oxidative stress. Free Radical Biology & Medicine, 23:90-99, 1997.
Holzel, R.; Calander, N.; Chiragwandi, Z; Wil ander, M.; Bier, F.F. Trapping Single Molecules by Dielectrophoresis. Phys. Rev. Left. 95:128102 (2005).
Huang Y, Ewalt Kl, Tirado M, Haigis R, Forster A, Ackley D, Heller MJ, O'Connell JP, and Krhak M, "Electric Manipulation ofBioparic l es and Macromolecules on Microfabricated Electrodes", Analytical Chemistry 2001, (73):1549-59.
Huang Y, Joo S, Duhon M, Heller MJ, Wallace B and Xu, "Dielectrophoretic Cell Separation 20 and Gene Expression Profiling on Microelectronic Chip Arrays", Analytical Chern. 2002, 74, 3362-71.
Hughes, Michael P., "Nanoparticle Manipulation by Electrostatic Forces," Handbook of Nanoscience, Engineering & Technology $2^{nd}$ Ed., Wa Goddard III, DW Brenner, S. Lyshenski & G. Iafrate (eds.) (CRC Press 2007), pp. 16-1 to 16-32.
JP2011-503234 Office action dated Mar. 5, 2013.
Krishnan et al., "Alternating current electrokinetic separation and detection of DNA nanoparticles in high-conductance solutions," Electrophoresis, 29(9): 1765-1774 (2008).
Krishnan et al., "An AC electrokinetic method for enhanced detection of DNA nanoparticles." J. Biophotonics,Apr;2(4):253-61 (2009).
Krishnan et al., "Interaction of nanoparticles at the DEP microelectrode interface under high conductance conditions," Electrochem. Comm., 11(8):1661-1666 (2009).
Morgan, H.; Hughes, M.P.; Green, N.G. "Separation of Sub micron Bioparticles by Dielectrophoresis" Biophysical Journal.77:516-525. 1999.
Nakagawa, et al. "Fabrication of amino Silane-Coated Microchip for DNA extraction from Whole Blood." Journal of Biotechnology, vol. 116, No. 2, 105-111 (2005).
PCT/US2009/039565 International Preliminary Report on Patentability and Written Opinion dated Oct. 5, 2010.
PCT/US2009/039565 International Search Report dated Dec. 23, 2009.
PCT/US2013/036845 International Search Report and Written Opinion dated Aug. 6, 2013.

Pethig R. "Dielectrophoresis: Using Inhomogenous AC Electrical Fields to Separate and Manipulate Cells," CRC Critical Reviews in Biotechnology, CRC Press, Boca Raton, FL, US, vol. 16, No. 4, Jan. 1, 1996, pp. 331-348 (XP009009220).
Ramos, A.; Morgan, H.; Green, N. G.; Castellanos, A. Ac electrokinetics: a review of forces in microelectrode structures. J Phys. D: Appl. Phys. 31:2338-2353; 1998.
Sonnenberg, et al. "Dielectrophoretic Isolation of DNA and Nonoparticles from Blood." Electrophoresis, vol. 33, No. 16, 2482-2490 (2012).
Stephens M, Talary MS, Pethig R, Burett AK, Mils KI. The dielectrophoresis enrichment of CD34+ cells from peripheral blood stern cell harvests. Bone Marrow Transplant. 18:777-782 (1996).
Stroun M, Aner P, Lyautey J, et aL. Isolation and characterization of DNA from the plasma of cancer patients. Eur J Cancer Clin Oneol 23:707-712. 1987.
Toner, et al. "Blood-on-a-chip." Annual Review of Biomedical Engineering, vol. 7, 77-103 (2005).
Tong, Y-K.; Lo, Y. M. D. Diagnostic developments involving cell-free (circulating) nucleic acids. Clinica Chimica Acta. 363:187-96; 2006.
Tuukanen, S.; Toppar, J. J.; Kuzyk, A.; Hirviniemi, L.; Hytonen, V. P.; Ilalainen T.; Torma, P. Carbon nanotubes as electrodes for dielectrophoresis of DNA. Nano Letters. 6:1339-1343; 2006.
U.S. Appl. No. 14/063,884 Office Action dated Feb. 12, 2014.
U.S. Appl. No. 12/936,147 Office Action dated Dec. 11, 2012.
U.S. Appl. No. 12/936,147 Office Action dated Oct. 31, 2012.
U.S. Appl. No. 12/936,147 Office Action dated Jul. 18, 2013.
U.S. Appl. No. 13/864,179 Office Action dated Aug. 15, 2013.
Washizu, M.; Kurosawa, 0. Electrostatic manipulation of DNA in micro fabricated structures. Industry Applications, IEEE Transactions on. 26:1165-1172; 1990.
Washizu, M.; Kurosawa, 0.; Arai, I.; Suzuki, S.; Shimamoto, N Applications of electrostatic stretch-and-positioning of DNA. Industry Applications, IEEE Transactions on. 31:447-456; 1995.
Wu et al, "Cell-free DNA: measurement in various carcinomas and establishment of normal reference range." Clin Chim Acta., 321(1-2):77-87 (2002).
Wu TL, Zhang D, Chia JH, Tsao KH, Sun CF, Wu JT. Cell-free DNA: measurement in varous carcinomas and establishment of normal reference range. Clin Chim Acta. 21:77-87. 2002.
Ziegler A, Zangemeister-Wittke D, Stahel Ra. Circulating DNA: a new diagnostic gold mine? Cancer Treat Rev. 5:255-71. 2002.
Hughes and Morgan, "Dielectrophoretic Characterization and Separation of Antibody-Coated Submicrometer Latex Spheres," Anal Chem., 1999, 71: 3441-3445.
Hughes et al., "Dielectrophoretic Manipulation and Characterization of Herpes Simplex Virus-1 Capsids," Eur Biophys J, 2001, 30: 268-272.
Hughes, "Strategies for Dielectrophoretic Separation in Laboratory-on-a-chip Systems," Electrophoresis, 2002, 23: 2569-2582.
Office Action in Japanese Application No. 2013-119141, dated Jun. 3, 2014, 2 pages (Partial English Translation).
U.S. Appl. No. 14/194,566 Office Action dated May 15, 2014.
U.S. Appl. No. 14/201,715 Office Action dated May 15, 2014.
U.S. Appl. No. 14/271,337 Office Action dated Jun. 12, 2014.

epsilonS(1)=2.5 Arrow: Electric Field Surface: $(m*kg^2/(s^6*A^2))$ Surface Marker: gradEE*(y>0.9e-6) $(m*kg^2/(s^6*A^2))$

NUCLEIC ACID SAMPLE PREPARATION

CROSS-REFERENCE

This application is a continuation of U.S. application Ser. No. 14/067,841, filed Oct. 30, 2013, which is a continuation of U.S. application Ser. No. 13/864,179, filed Apr. 16, 2013, which claims the benefit of U.S. Provisional Application No. 61/624,897, filed Apr. 16, 2012, which application is incorporated herein by reference.

BACKGROUND OF THE INVENTION

Exponentially rapid progress has been made in the field of DNA sequencing in recent years. Methods such as pyrosequencing, ion semiconductor sequencing and polony sequencing aim to reduce costs to a point where sequencing a complete genome becomes routine. This is expected to transform fields as diverse as medicine, renewable energy, biosecurity and agriculture to name a few. However, techniques for isolating DNA suitable for sequencing have not kept pace and there is a threat that this will become a limitation.

SUMMARY OF THE INVENTION

In some instances, the present invention fulfills a need for improved methods of nucleic acid isolation from biological samples. Particular attributes of certain aspects provided herein include a total sample preparation time of less than about one hour, with hands-on time of less than about one minute. In some embodiments, the present invention can be used to isolate DNA from dilute and/or complex fluids such as blood or environmental samples. In other aspects, the present invention can use small amounts of starting material, achieve highly purified nucleic acids, and is amenable to multiplexed and high-throughput operation.

Disclosed herein, in some embodiments, is a method for isolating a nucleic acid from a fluid comprising cells, the method comprising: a. applying the fluid to a device, the device comprising an array of electrodes capable of establishing an AC electrokinetic field region; b. concentrating a plurality of cells in a first AC electrokinetic field region, wherein the first AC eletrokinetic field region is a first dielectrophoretic high field region and the conductivity of the fluid is less than 500 mS/m; c. lysing the cells on the array; and d. isolating nucleic acid in a second AC electrokinetic field region, wherein the second AC electrokinetic field is a second dielectrophoretic high field region. In some embodiments, the AC electrokinetic field is produced using an alternating current having a voltage of 1 volt to 40 volts peak-peak, and/or a frequency of 5 Hz to 5,000,000 Hz and duty cycles from 5% to 50%. In some embodiments, the conductivity of the fluid is less than 300 mS/m. In some embodiments, the electrodes are selectively energized to provide the first dielectrophoretic high field region and subsequently or continuously selectively energized to provide the second dielectrophoretic high field region. In some embodiments, the cells are lysed using a direct current, a chemical lysing agent, an enzymatic lysing agent, heat, pressure, sonic energy, or a combination thereof. In some embodiments, the method further comprises degradation of residual proteins after cell lysis. In some embodiments, the cells are lysed using a direct current with a voltage of 1-500 volts, a pulse frequency of 0.2 to 200 Hz with duty cycles from 10-50%, and a pulse duration of 0.01 to 10 seconds applied at least once. In some embodiments, the array of electrodes is spin-coated with a hydrogel having a thickness between about 0.1 microns and 1 micron. In some embodiments, the hydrogel comprises two or more layers of a synthetic polymer. In some embodiments, the hydrogel has a viscosity between about 0.5 cP to about 5 cP prior to spin-coating. In some embodiments, the hydrogel has a conductivity between about 0.1 S/m to about 1.0 S/m. In some embodiments, the isolated nucleic acid comprises less than about 10% non-nucleic acid cellular material or cellular protein by mass. In some embodiments, the method is completed in less than 10 minutes. In some embodiments, the array of electrodes comprises a wavy line configuration, wherein the configuration comprises a repeating unit comprising the shape of a pair of dots connected by linker, wherein the linker tapers inward toward the midpoint between the pair of dots, wherein the diameters of the dots are the widest points along the length of the repeating unit, wherein the edge to edge distance between a parallel set of repeating units is equidistant, or roughly equidistant. In some embodiments, the array of electrodes comprises a passivation layer with a relative electrical permittivity from about 2.0 to about 4.0.

In some embodiments, disclosed herein is a method for isolating a nucleic acid from a fluid comprising cells, the method comprising: a. applying the fluid to a device, the device comprising an array of electrodes capable of establishing an AC electrokinetic field region; b. concentrating a plurality of cells in a first AC electrokinetic field region, wherein the first AC electrokinetic field region is a first dielectrophoretic low field region and the conductivity of the fluid is greater than 300 mS/m; c. isolating nucleic acid in a second AC electrokinetic field region, wherein the second AC electrokinetic field is a second eletrophoretic high field region; and d. flushing cells away from the array. In some embodiments, the AC electrokinetic field is produced using an alternating current having a voltage of 1 volt to 40 volts peak-peak, and/or a frequency of 5 Hz to 5,000,000 Hz and duty cycles from 5% to 50%. In some embodiments, the conductivity of the fluid is greater than 500 mS/m. In some embodiments, the electrodes are selectively energized to provide the first dielectrophoretic high field region and subsequently or continuously selectively energized to provide the second dielectrophoretic high field region. In some embodiments, the method further comprises degrading residual proteins on the array. In some embodiments, the residual proteins are degraded by one or more of a chemical degradant or an enzymatic degradant. In some embodiments, the residual proteins are degraded by Proteinase K. In some embodiments, the array of electrodes is spin-coated with a hydrogel having a thickness between about 0.1 microns and 1 micron. In some embodiments, the hydrogel comprises two or more layers of a synthetic polymer. In some embodiments, the hydrogel has a viscosity between about 0.5 cP to about 5 cP prior to spin-coating. In some embodiments, the hydrogel has a conductivity between about 0.1 S/m to about 1.0 S/m. In some embodiments, the isolated nucleic acid comprises less than about 10% non-nucleic acid cellular material or cellular protein by mass. In some embodiments, the method is completed in less than 10 minutes. In some embodiments, the array of electrodes comprises a wavy line configuration, wherein the configuration comprises a repeating unit comprising the shape of a pair of dots connected by linker, wherein the linker tapers inward toward the midpoint between the pair of dots, wherein the diameters of the dots are the widest points along the length of the repeating unit, wherein the edge to edge distance between a parallel set of repeating units is equidistant, or roughly equidistant. In some embodiments, the array of electrodes comprises a passivation layer with a relative electrical permittivity from about 2.0 to about 4.0.

Disclosed herein, in some embodiments, is a method for isolating a nucleic acid from a fluid comprising cells, the method comprising: a. applying the fluid to a device, the device comprising an array of electrodes capable of generating an AC electrokinetic field; b. concentrating a plurality of cells in a first AC electrokinetic field region; c. lysing the cells in the first AC electrokinetic field region; and d. isolating the nucleic acid in a second AC electrokinetic field region, wherein the fluid is at a conductivity capable of concentrating a plurality of cells in the first AC electrokinetic field region. In some embodiments, the first AC electrokinetic region is a dielectrophoretic field region, wherein the second AC electrokinetic field region is a dielectrophoretic field region, or a combination thereof. In some embodiments, the first AC electrokinetic field region is a first dielectrophoretic low field region and the second AC electrokinetic field region is a second dielectrophoretic high field region, wherein the conductivity of the fluid is greater than 300 mS/m. In some embodiments, the first AC electrokinetic field region is a first dielectrophoretic high field region and the second AC electrokinetic field region is a second dielectrophoretic high field region, wherein the conductivity of the fluid is less than 300 mS/m. In some embodiments, the nucleic acid is concentrated in the second AC electrokinetic field region. In some embodiments, the method further comprises flushing residual material from the array and the isolated nucleic acid. In some embodiments, the method further comprises degradation of a residual protein. In some embodiments, the method further comprises flushing degraded proteins from the array and the isolated nucleic acid. In some embodiments, the method further comprises collecting the nucleic acid. In some embodiments, the first AC electrokinetic field region is produced by an alternating current. In some embodiments, the first AC electrokinetic field region is produced using an alternating current having a voltage of 1 volt to 40 volts peak-peak; and/or a frequency of 5 Hz to 5,000,000 Hz, and duty cycles from 5% to 50%. In some embodiments, the second AC electrokinetic field region is a different region of the electrode array as the first AC electrokinetic field region. In some embodiments, the second AC electrokinetic field region is the same region of the electrode array as the first AC electrokinetic field region. In some embodiments, the second AC electrokinetic field region is produced by an alternating current. In some embodiments, the second AC electrokinetic field region is produced using an alternating current having a voltage of 1 volt to 50 volts peak-peak; and/or a frequency of 5 Hz to 5,000,000 Hz, and duty cycles from 5% to 50%. In some embodiments, the electrodes are selectively energized to provide the first AC electrokinetic field region and subsequently or continuously selectively energized to provide the second AC electrokinetic field region. In some embodiments, the cells are lysed by applying a direct current to the cells. In some embodiments, the direct current used to lyse the cells has a voltage of 1-500 volts; and a duration of 0.01 to 10 seconds applied once or as multiple pulses. In some embodiments, the direct current used to lyse the cells is a direct current pulse or a plurality of direct current pulses applied at a frequency suitable for lysing the cells. In some embodiments, the pulse has a frequency of 0.2 to 200 Hz with duty cycles from 10-50%. In some embodiments, the cells are lysed on the device using a direct current, a chemical lysing agent, an enzymatic lysing agent, heat, osmotic pressure, sonic energy, or a combination thereof. In some embodiments, the residual material comprises lysed cellular material. In some embodiments, the lysed cellular material comprises residual protein freed from the plurality of cells upon lysis. In some embodiments, the array of electrodes is coated with a hydrogel. In some embodiments, the hydrogel comprises two or more layers of a synthetic polymer. In some embodiments, the hydrogel is spin-coated onto the electrodes. In some embodiments, the hydrogel has a viscosity between about 0.5 cP to about 5 cP prior to spin-coating. In some embodiments, the hydrogel has a thickness between about 0.1 microns and 1 micron. In some embodiments, the hydrogel has a conductivity between about 0.1 S/m to about 1.0 S/m. In some embodiments, the array of electrodes is in a dot configuration. In some embodiments, the angle of orientation between dots is from about 25° to about 60°. In some embodiments, the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant. In some embodiments, the array of electrodes comprises a passivation layer with a relative electrical permittivity from about 2.0 to about 4.0. In some embodiments, the method further comprises amplifying the isolated nucleic acid by polymerase chain reaction. In some embodiments, the nucleic acid comprises DNA, RNA, or any combination thereof. In some embodiments, the isolated nucleic acid comprises less than about 80%, less than about 70%, less than about 60%, less than about 50%, less than about 40%, less than about 30%, less than about 20%, less than about 10%, less than about 5%, or less than about 2% non-nucleic acid cellular material and/or protein by mass. In some embodiments, the isolated nucleic acid comprises greater than about 99%, greater than about 98%, greater than about 95%, greater than about 90%, greater than about 80%, greater than about 70%, greater than about 60%, greater than about 50%, greater than about 40%, greater than about 30%, greater than about 20%, or greater than about 10% nucleic acid by mass. In some embodiments, the method is completed in less than about one hour. In some embodiments, centrifugation is not used. In some embodiments, the residual proteins are degraded by one or more of chemical degradation and enzymatic degradation. In some embodiments, the residual proteins are degraded by Proteinase K. In some embodiments, the residual proteins are degraded by an enzyme, the method further comprising inactivating the enzyme following degradation of the proteins. In some embodiments, the enzyme is inactivated by heat (e.g., 50 to 95° C. for 5-15 minutes). In some embodiments, the residual material and the degraded proteins are flushed in separate or concurrent steps. In some embodiments, the isolated nucleic acid is collected by (i) turning off the second AC electrokinetic field region; and (ii) eluting the nucleic acid from the array in an eluant. In some embodiments, nucleic acid is isolated in a form suitable for sequencing. In some embodiments, the nucleic acid is isolated in a fragmented form suitable for shotgun-sequencing. In some embodiments, the fluid comprising cells has a low conductivity or a high conductivity. In some embodiments, the fluid comprises a bodily fluid, blood, serum, plasma, urine, saliva, a food, a beverage, a growth medium, an environmental sample, a liquid, water, clonal cells, or a combination thereof. In some embodiments, the cells comprise clonal cells, pathogen cells, bacteria cells, viruses, plant cells, animal cells, insect cells, and/or combinations thereof. In some embodiments, the method further comprises sequencing the isolated nucleic acid. In some embodiments, the nucleic acid is sequenced by Sanger sequencing, pyrosequencing, ion semiconductor sequencing, polony sequencing, sequencing by ligation, DNA nanoball sequencing, sequencing by ligation, or single molecule sequencing. In some embodiments, the method further comprises performing a reaction on the DNA (e.g., fragmentation, restriction digestion, ligation). In some embodiments, the reaction occurs on or near the array or in the device. In some embodiments, the fluid comprising cells comprises no more than 10,000 cells.

Disclosed herein, in some embodiments, is a method for isolating a nucleic acid from a fluid comprising cells, the method comprising: a. applying the fluid to a device, the device comprising an array of electrodes capable of generating an AC electrokinetic field; b. concentrating a plurality of cells in a first AC electrokinetic (e.g., dielectrophoretic) field region; c. isolating nucleic acid in a second AC electrokinetic (e.g., dielectrophoretic) field region; and d. flushing cells away, wherein the fluid is at a conductivity capable of concentrating a plurality of cells in the first AC electrokinetic field region. In some embodiments, the first AC electrokinetic field region is a dielectrophoretic field region. In some embodiments, the first AC electrokinetic field region is a dielectrophoretic low field region, and wherein the fluid conductivity is greater than 300 mS/m. In some embodiments, the second AC electrokinetic field region is a dielectrophoretic field region. In some embodiments, the method further comprises degradation of residual proteins after step (e). In some embodiments, the method further comprises flushing the degraded proteins from the nucleic acid. In some embodiments, the method further comprises collecting the nucleic acid. In some embodiments, the first AC electrokinetic field region is produced by an alternating current. In some embodiments, the first AC electrokinetic field region is produced using an alternating current having a voltage of 1 volt to 40 volts peak-peak; and/or a frequency of 5 Hz to 5,000,000 Hz, and duty cycles from 5% to 50%. In some embodiments, the second AC electrokinetic field region is a different region of the electrode array as the first AC electrokinetic field region. In some embodiments, the second AC electrokinetic field region is the same region of the electrode array as the first AC electrokinetic field region. In some embodiments, the second AC electrokinetic field region is produced by an alternating current. In some embodiments, the second AC electrokinetic field region is a dielectrophoretic high field region. In some embodiments, the second AC electrokinetic field region is produced using an alternating current having a voltage of 1 volt to 50 volts peak-peak; and/or a frequency of 5 Hz to 5,000,000 Hz, and duty cycles from 5% to 50%. In some embodiments, the electrodes are selectively energized to provide the first AC electrokinetic field region and subsequently or continuously selectively energized to provide the second AC electrokinetic field region. In some embodiments, the array of electrodes is coated with a hydrogel. In some embodiments, the hydrogel comprises two or more layers of a synthetic polymer. In some embodiments, the hydrogel is spin-coated onto the electrodes. In some embodiments, the hydrogel has a viscosity between about 0.5 cP to about 5 cP prior to spin-coating. In some embodiments, the hydrogel has a thickness between about 0.1 microns and 1 micron. In some embodiments, the hydrogel has a conductivity between about 0.1 S/m to about 1.0 S/m. In some embodiments, the array of electrodes is in a dot configuration. In some embodiments, the angle of orientation between dots is from about 25° to about 60°. In some embodiments, the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant. In some embodiments, the array of electrodes comprises a passivation layer with a relative electrical permittivity from about 2.0 to about 4.0. In some embodiments, the method further comprises amplifying the isolated nucleic acid by polymerase chain reaction. In some embodiments, the nucleic acid comprises DNA, RNA, or any combination thereof. In some embodiments, the isolated nucleic acid comprises less than about 80%, less than about 70%, less than about 60%, less than about 50%, less than about 40%, less than about 30%, less than about 20%, less than about 10%, less than about 5%, or less than about 2% non-nucleic acid cellular material and/or protein by mass. In some embodiments, the isolated nucleic acid comprises greater than about 99%, greater than about 98%, greater than about 95%, greater than about 90%, greater than about 80%, greater than about 70%, greater than about 60%, greater than about 50%, greater than about 40%, greater than about 30%, greater than about 20%, or greater than about 10% nucleic acid by mass. In some embodiments, the method is completed in less than about one hour. In some embodiments, centrifugation is not used. In some embodiments, the residual proteins are degraded by one or more of chemical degradation and enzymatic degradation. In some embodiments, the residual proteins are degraded by Proteinase K. In some embodiments, the residual proteins are degraded by an enzyme, the method further comprising inactivating the enzyme following degradation of the proteins. In some embodiments, the enzyme is inactivated by heat (e.g., 50 to 95° C. for 5-15 minutes). In some embodiments, the residual material and the degraded proteins are flushed in separate or concurrent steps. In some embodiments, the isolated nucleic acid is collected by (i) turning off the second AC electrokinetic field region; and (ii) eluting the nucleic acid from the array in an eluant. In some embodiments, nucleic acid is isolated in a form suitable for sequencing. In some embodiments, the nucleic acid is isolated in a fragmented form suitable for shotgun-sequencing. In some embodiments, the fluid comprising cells has a low conductivity or a high conductivity. In some embodiments, the fluid comprises a bodily fluid, blood, serum, plasma, urine, saliva, a food, a beverage, a growth medium, an environmental sample, a liquid, water, clonal cells, or a combination thereof. In some embodiments, the cells comprise clonal cells, pathogen cells, bacteria cells, viruses, plant cells, animal cells, insect cells, and/or combinations thereof. In some embodiments, the method further comprises sequencing the isolated nucleic acid. In some embodiments, the nucleic acid is sequenced by Sanger sequencing, pyrosequencing, ion semiconductor sequencing, polony sequencing, sequencing by ligation, DNA nanoball sequencing, sequencing by ligation, or single molecule sequencing. In some embodiments, the method further comprises performing a reaction on the DNA (e.g., fragmentation, restriction digestion, ligation). In some embodiments, the reaction occurs on or near the array or in the device. In some embodiments, the fluid comprising cells comprises no more than 10,000 cells.

In some embodiments, disclosed herein is a device for isolating a nucleic acid from a fluid comprising cells, the device comprising: a. a housing; b. a heater and/or a reservoir comprising a protein degradation agent; and c. a plurality of alternating current (AC) electrodes within the housing, the AC electrodes configured to be selectively energized to establish AC electrokinetic high field and AC electrokinetic low field regions, whereby AC electrokinetic effects provide for concentration of cells in low field regions of the device. In some embodiments, the plurality of electrodes is configured to be selectively energized to establish a dielectrophoretic high field and dielectrophoretic low field regions. In some embodiments, the array of electrodes is coated with a hydrogel. In some embodiments, the hydrogel comprises two or more layers of a synthetic polymer. In some embodiments, the hydrogel is spin-coated onto the electrodes. In some embodiments, the hydrogel has a viscosity between about 0.5 cP to about 5 cP prior to spin-coating. In some embodiments, the hydrogel has a thickness between about 0.1 microns and 1 micron. In some embodiments, the hydrogel has a conductivity between about 0.1 S/m to about 1.0 S/m. In some embodiments, the array of electrodes is in a dot configuration. In some embodiments, the angle of orientation between dots is from about 25° to about 60°. In some embodiments, the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant. In some embodiments, the array of electrodes comprises a passivation layer with a relative electrical permittivity from about 2.0 to about 4.0. In some embodiments, the protein degradation agent is Proteinase K. In some embodiments, the device further comprises a second reservoir comprising an eluant.

In some embodiments, disclosed herein is a system for isolating a nucleic acid from a fluid comprising cells, the system comprising: a. a device comprising a plurality of alternating current (AC) electrodes, the AC electrodes configured to be selectively energized to establish AC electrokinetic high field and AC electrokinetic low field regions, whereby AC electrokinetic effects provide for concentration of cells in high field regions of the device, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant; and b. a module capable of sequencing DNA by Sanger sequencing or next generation sequencing methods; c. a software program capable of controlling the device comprising a plurality of AC electrodes, the module capable of sequencing DNA or a combination thereof; and d. a fluid comprising cells. In some embodiments, the plurality of electrodes is configured to be selectively energized to establish a dielectrophoretic high field and dielectrophoretic low field regions.

Disclosed herein, in some embodiments, is a device comprising: a. a plurality of alternating current (AC) electrodes, the AC electrodes configured to be selectively energized to establish AC electrokinetic high field and AC electrokinetic low field regions, wherein the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant; and b. a module capable of thermocycling and amplifying nucleic acids. In some embodiments, the plurality of electrodes is configured to be selectively energized to establish a dielectrophoretic high field and dielectrophoretic low field regions. In some embodiments, the device is capable of isolating nucleic acids from a fluid comprising cells and performing amplification of the isolated nucleic acids. In some embodiments, the isolated nucleic acid is DNA or mRNA. In some embodiments, nucleic acid is isolated and amplification is performed in a single chamber. In some embodiments, nucleic acid is isolated and amplification is performed in multiple regions of a single chamber. In some embodiments, the device further comprises using at least one of an elution tube, a chamber and a reservoir to perform amplification. In some embodiments, amplification of the nucleic acid is polymerase chain reaction (PCR)-based. In some embodiments, amplification of the nucleic acid is performed in a serpentine microchannel comprising a plurality of temperature zones. In some embodiments, amplification is performed in aqueous droplets entrapped in immiscible fluids (i.e., digital PCR). In some embodiments, the thermocycling comprises convection. In some embodiments, the device comprises a surface contacting or proximal to the electrodes, wherein the surface is functionalized with biological ligands that are capable of selectively capturing biomolecules. In some embodiments, the array of electrodes is coated with a hydrogel. In some embodiments, the hydrogel comprises two or more layers of a synthetic polymer. In some embodiments, the hydrogel is spin-coated onto the electrodes. In some embodiments, the hydrogel has a viscosity between about 0.5 cP to about 5 cP prior to spin-coating. In some embodiments, the hydrogel has a thickness between about 0.1 microns and 1 micron. In some embodiments, the hydrogel has a conductivity between about 0.1 S/m to about 1.0 S/m. In some embodiments, the array of electrodes comprises a passivation layer with a relative electrical permittivity from about 2.0 to about 4.0. In some embodiments, the surface selectively captures biomolecules by: a. nucleic acid hybridization; b. antibody-antigen interactions; c. biotin-avidin interactions; d. ionic or electrostatic interactions; or e. any combination thereof. In some embodiments, the surface is functionalized to minimize and/or inhibit nonspecific binding interactions by: a. polymers (e.g., polyethylene glycol PEG); b. ionic or electrostatic interactions; c.

surfactants; or d. any combination thereof. In some embodiments, the device comprises a plurality of microelectrode devices oriented (a) flat side by side, (b) facing vertically, or (c) facing horizontally. In some embodiments, the device comprises a module capable of performing Sanger sequencing. In some embodiments, the module capable of performing Sanger sequencing comprises a module capable of capillary electrophoresis, a module capable of multi-color fluorescence detection, or a combination thereof.

Disclosed herein, in some embodiments, is a device comprising: a. a plurality of alternating current (AC) electrodes, the AC electrodes configured to be selectively energized to establish AC electrokinetic high field and AC electrokinetic low field regions, wherein the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant; and b. a module capable of performing sequencing. In some embodiments, the plurality of electrodes is configured to be selectively energized to establish a dielectrophoretic high field and dielectrophoretic low field regions. In some embodiments, the device comprises a surface contacting or proximal to the electrodes, wherein the surface is functionalized with biological ligands that are capable of selectively capturing biomolecules. In some embodiments, the array of electrodes is coated with a hydrogel. In some embodiments, the hydrogel comprises two or more layers of a synthetic polymer. In some embodiments, the hydrogel is spin-coated onto the electrodes. In some embodiments, the hydrogel has a viscosity between about 0.5 cP to about 5 cP prior to spin-coating. In some embodiments, the hydrogel has a thickness between about 0.1 microns and 1 micron. In some embodiments, the hydrogel has a conductivity between about 0.1 S/m to about 1.0 S/m. In some embodiments, the array of electrodes comprises a passivation layer with a relative electrical permittivity from about 2.0 to about 4.0. In some embodiments, the surface selectively captures biomolecules by: a. nucleic acid hybridization; b. antibody-antigen interactions; c. biotin-avidin interactions; d. ionic or electrostatic interactions; or e. any combination thereof. In some embodiments, the surface is functionalized to minimize and/or inhibit nonspecific binding interactions by: a. polymers (e.g., polyethylene glycol PEG); b. ionic or electrostatic interactions; c. surfactants; or d. any combination thereof. In some embodiments, the device comprises a plurality of microelectrode devices oriented (a) flat side by side, (b) facing vertically, or (c) facing horizontally. In some embodiments, the device comprises a module capable of performing next generation sequencing. In some embodiments, the module capable of performing next-generation sequencing is capable of performing pyrosequencing, ion semiconductor sequencing, polony sequencing, sequencing by ligation, DNA nanoball sequencing, or single molecule sequencing.

Disclosed herein, in some embodiments, is a method of isolating a nucleic acid from a fluid comprising cells, comprising a) performing a method disclosed herein; b) performing PCR amplification on the nucleic acid, or a cDNA version of the nucleic acid, to produce a PCR product; c) isolating the PCR product in a third AC electrokinetic region; d) performing Sanger chain termination reactions on the PCR product to produce a sequencing product of the nucleic acid; and e) performing electrophoretic separation of the sequencing product of the nucleic acid. In some embodiments, the third AC electrokinetic region is a dielectrophoretic field region. In some embodiments, the third AC electrokinetic region is a dielectrophoretic high field region. In some embodiments, the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant. In some embodiments, the electrophoretic separation of the sequencing product of the nucleic acid is capillary electrophoresis. In some embodiments, the method further comprises the use of multicolor fluorescence detection to analyze the sequencing product of the nucleic acid. In some embodiments, all steps are performed on a single chip. In some embodiments, the fluid comprising cells comprises no more than 10,000 cells.

Incorporation by Reference

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
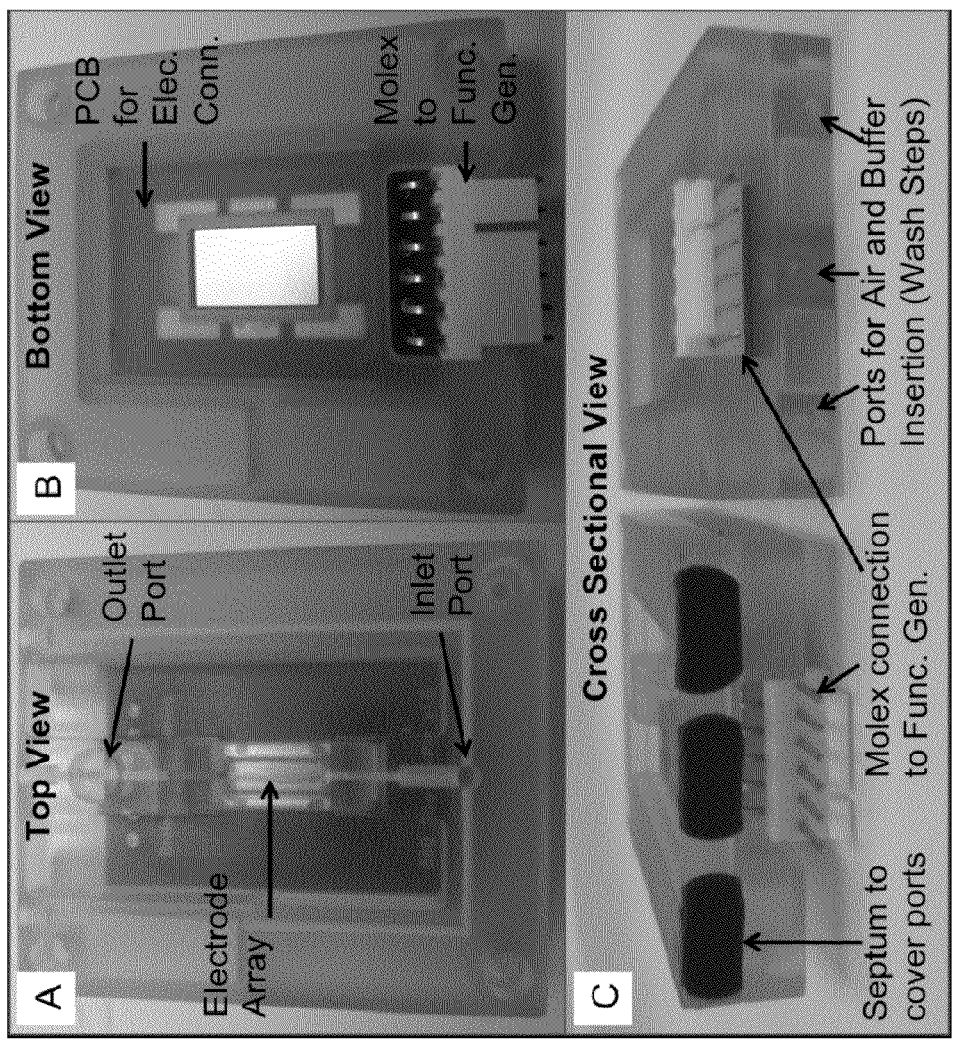
FIG. 1 shows a top view (A), a bottom view (B) and a cross-sectional view (C) of an exemplary device.

Described herein are methods, devices and systems suitable for isolating or separating particles or molecules from a fluid composition. In specific embodiments, provided herein are methods, devices and systems for isolating or separating a nucleic acid from a fluid comprising cells or other particulate material. In some aspects, the methods, devices and systems may allow for rapid separation of particles and molecules in a fluid composition. In other aspects, the methods, devices and systems may allow for rapid isolation of molecules from particles in a fluid composition. In various aspects, the methods, devices and systems may allow for a rapid procedure that requires a minimal amount of material and/or results in high purity DNA isolated from complex fluids such as blood or environmental samples.

Provided in certain embodiments herein are methods, devices and systems for isolating or separating particles or molecules from a fluid composition, the methods, devices, and systems comprising applying the fluid to a device comprising an array of electrodes and being capable of generating AC electrokinetic forces (e.g., when the array of electrodes are energized). In some embodiments, the dielectrophoretic field, is a component of AC electrokinetic force effects. In other embodiments, the component of AC electrokinetic force effects is AC electroosmosis or AC electrothermal effects. In some embodiments the AC electrokinetic force, including dielectrophoretic fields, comprises high-field regions (positive DEP, i.e. area where there is a strong concentration of electric field lines due to a non-uniform electric field) and/or low-field regions (negative DEP, i.e. area where there is a weak concentration of electric field lines due to a non-uniform electric field).

In specific instances, the particles or molecules (e.g., nucleic acid) are isolated (e.g., isolated or separated from cells) in a field region (e.g., a high field region) of the dielectrophoretic field. In some embodiments, the method, device, or system further includes one or more of the following steps: concentrating cells of interest in a first dielectrophoretic field region (e.g., a high field DEP region), lysing cells in the first dielectrophoretic field region, and/or concentrating nucleic acid in a first or second dielectrophoretic field region. In other embodiments, the method, device, or system includes one or more of the following steps: concentrating cells in a first dielectrophoretic field region (e.g., a low field DEP region), concentrating nucleic acid in a second dielectrophoretic field region (e.g., a high field DEP region), and washing away the cells and residual material. The method also optionally includes devices and/or systems capable of performing one or more of the following steps: washing or otherwise removing residual (e.g., cellular) material from the nucleic acid (e.g., rinsing the array with water or buffer while the nucleic acid is concentrated and maintained within a high field DEP region of the array), degrading residual proteins (e.g., residual proteins from lysed cells and/or other sources, such degradation occurring according to any suitable mechanism, such as with heat, a protease, or a chemical), flushing degraded proteins from the nucleic acid, and collecting the nucleic acid. In some embodiments, the result of the methods, operation of the devices, and operation of the systems described herein is an isolated nucleic acid, optionally of suitable quantity and purity for DNA sequencing.

In some instances, it is advantageous that the methods described herein are performed in a short amount of time, the devices are operated in a short amount of time, and the systems are operated in a short amount of time. In some embodiments, the period of time is short with reference to the "procedure time" measured from the time between adding the fluid to the device and obtaining isolated nucleic acid. In some embodiments, the procedure time is less than 3 hours, less than 2 hours, less than 1 hour, less than 30 minutes, less than 20 minutes, less than 10 minutes, or less than 5 minutes.

In another aspect, the period of time is short with reference to the "hands-on time" measured as the cumulative amount of time that a person must attend to the procedure from the time between adding the fluid to the device and obtaining isolated nucleic acid. In some embodiments, the hands-on time is less than 20 minutes, less than 10 minutes, less than 5 minute, less than 1 minute, or less than 30 seconds.

In some instances, it is advantageous that the devices described herein comprise a single vessel, the systems described herein comprise a device comprising a single vessel and the methods described herein can be performed in a single vessel, e.g., in a dielectrophoretic device as described herein. In some aspects, such a single-vessel embodiment minimizes the number of fluid handling steps and/or is performed in a short amount of time. In some instances, the present methods, devices and systems are contrasted with methods, devices and systems that use one or more centrifugation steps and/or medium exchanges. In some instances, centrifugation increases the amount of hands-on time required to isolate nucleic acids. In another aspect, the single-vessel procedure or device isolates nucleic acids using a minimal amount of consumable reagents.

Devices and Systems

In some embodiments, described herein are devices for collecting a nucleic acid from a fluid. In one aspect, described herein are devices for collecting a nucleic acid from a fluid comprising cells or other particulate material. In other aspects, the devices disclosed herein are capable of collecting and/or isolating nucleic acid from a fluid comprising cellular or protein material. In other instances, the devices disclosed herein are capable of collecting and/or isolating nucleic acid from cellular material.

In some embodiments, disclosed herein is a device for isolating a nucleic acid from a fluid comprising cells or other particulate material, the device comprising: a. a housing; b. a heater or thermal source and/or a reservoir comprising a protein degradation agent; and c. a plurality of alternating current (AC) electrodes within the housing, the AC electrodes configured to be selectively energized to establish AC electrokinetic high field and AC electrokinetic low field regions, whereby AC electrokinetic effects provide for concentration of cells in low field regions of the device. In some embodiments, the plurality of electrodes is configured to be selectively energized to establish a dielectrophoretic high field and dielectrophoretic low field regions. In some embodiments, the protein degradation agent is a protease. In some embodiments, the protein degradation agent is Proteinase K. In some embodiments, the device further comprises a second reservoir comprising an eluant.

In some embodiments, disclosed herein is a device comprising: a. a plurality of alternating current (AC) electrodes, the AC electrodes configured to be selectively energized to establish AC electrokinetic high field and AC electrokinetic low field regions; and b. a module capable of thermocycling and performing PCR or other enzymatic reactions. In some embodiments, the plurality of electrodes is configured to be selectively energized to establish a dielectrophoretic high field and dielectrophoretic low field regions. In some embodiments, the device is capable of isolating DNA from a fluid comprising cells and performing PCR amplification or other enzymatic reactions. In some embodiments, DNA is isolated and PCR or other enzymatic reaction is performed in a single chamber. In some embodiments, DNA is isolated and PCR or other enzymatic reaction is performed in multiple regions of a single chamber. In some embodiments, DNA is isolated and PCR or other enzymatic reaction is performed in multiple chambers.

In some embodiments, the device further comprises at least one of an elution tube, a chamber and a reservoir to perform PCR amplification or other enzymatic reaction. In some embodiments, PCR amplification or other enzymatic reaction is performed in a serpentine microchannel comprising a plurality of temperature zones. In some embodiments, PCR amplification or other enzymatic reaction is performed in aqueous droplets entrapped in immiscible fluids (i.e., digital PCR). In some embodiments, the thermocycling comprises convection. In some embodiments, the device comprises a surface contacting or proximal to the electrodes, wherein the surface is functionalized with biological ligands that are capable of selectively capturing biomolecules.

In some embodiments, disclosed herein is a system for isolating a nucleic acid from a fluid comprising cells or other particulate material, the system comprising: a. a device comprising a plurality of alternating current (AC) electrodes, the AC electrodes configured to be selectively energized to establish AC electrokinetic high field and AC electrokinetic low field regions, whereby AC electrokinetic effects provide for concentration of cells in high field regions of the device; and b. a sequencer, thermocycler or other device for performing enzymatic reactions on isolated or collected nucleic acid. In some embodiments, the plurality of electrodes is configured to be selectively energized to establish a dielectrophoretic high field and dielectrophoretic low field regions.

In various embodiments, DEP fields are created or capable of being created by selectively energizing an array of electrodes as described herein. The electrodes are optionally made of any suitable material resistant to corrosion, including metals, such as noble metals (e.g. platinum, platinum iridium alloy, palladium, gold, and the like). In various embodiments, electrodes are of any suitable size, of any suitable orientation, of any suitable spacing, energized or capable of being energized in any suitable manner, and the like such that suitable DEP and/or other electrokinetic fields are produced.

In some embodiments described herein are methods, devices and systems in which the electrodes are placed into separate chambers and positive DEP regions and negative DEP regions are created within an inner chamber by passage of the AC DEP field through pore or hole structures. Various geometries are used to form the desired positive DEP (high field) regions and DEP negative (low field) regions for carrying cellular, microparticle, nanoparticle, and nucleic acid separations. In some embodiments, pore or hole structures contain (or are filled with) porous material (hydrogels) or are covered with porous membrane structures. In some embodiments, by segregating the electrodes into separate chambers, such pore/hole structure DEP devices reduce electrochemistry effects, heating, or chaotic fluidic movement from occurring in the inner separation chamber during the DEP process.

In one aspect, described herein is a device comprising electrodes, wherein the electrodes are placed into separate chambers and DEP fields are created within an inner chamber by passage through pore structures. The exemplary device includes a plurality of electrodes and electrode-containing chambers within a housing. A controller of the device independently controls the electrodes, as described further in PCT patent publication WO 2009/146143 A2, which is incorporated herein for such disclosure.

In some embodiments, chambered devices are created with a variety of pore and/or hole structures (nanoscale, microscale and even macroscale) and contain membranes, gels or filtering materials which control, confine or prevent cells, nanoparticles or other entities from diffusing or being transported into the inner chambers while the AC/DC electric fields, solute molecules, buffer and other small molecules can pass through the chambers.

In various embodiments, a variety of configurations for the devices are possible. For example, a device comprising a larger array of electrodes, for example in a square or rectangular pattern configured to create a repeating non-uniform electric field to enable AC electrokinetics. For illustrative purposes only, a suitable electrode array may include, but is not limited to, a 10×10 electrode configuration, a 50×50 electrode configuration, a 10×100 electrode configuration, 20×100 electrode configuration, or a 20×80 electrode configuration.

Such devices include, but are not limited to, multiplexed electrode and chambered devices, devices that allow reconfigurable electric field patterns to be created, devices that combine DC electrophoretic and fluidic processes; sample preparation devices, sample preparation, enzymatic manipulation of isolated nucleic acid molecules and diagnostic devices that include subsequent detection and analysis, lab-on-chip devices, point-of-care and other clinical diagnostic systems or versions.

In some embodiments, a planar platinum electrode array device comprises a housing through which a sample fluid flows. In some embodiments, fluid flows from an inlet end to an outlet end, optionally comprising a lateral analyte outlet. The exemplary device includes multiple AC electrodes. In some embodiments, the sample consists of a combination of micron-sized entities or cells, larger nanoparticulates and smaller nanoparticulates or biomolecules. In some instances, the larger nanoparticulates are cellular debris dispersed in the sample. In some embodiments, the smaller nanoparticulates are proteins, smaller DNA, RNA and cellular fragments. In some embodiments, the planar electrode array device is a 60×20 electrode array that is optionally sectioned into three 20×20 arrays that can be separately controlled but operated simultaneously. The optional auxiliary DC electrodes can be switched on to positive charge, while the optional DC electrodes are switched on to negative charge for electrophoretic purposes. In some instances, each of the controlled AC and DC systems is used in both a continuous and/or pulsed manner (e.g., each can be pulsed on and off at relatively short time intervals) in various embodiments. The optional planar electrode arrays along the sides of the sample flow, when overlayered with nanoporous material (e.g., a hydrogel of synthetic polymer), are optionally used to generate DC electrophoretic forces as well as AC DEP. Additionally, microelectrophoretic separation processes is optionally carried out within the nanopore layers using planar electrodes in the array and/or auxiliary electrodes in the x-y-z dimensions.

In various embodiments these methods, devices and systems are operated in the AC frequency range of from 1,000 Hz to 100 MHz, at voltages which could range from approximately 1 volt to 2000 volts pk-pk; at DC voltages from 1 volt to 1000 volts, at flow rates of from 10 microliters per minute to 10 milliliter per minute, and in temperature ranges from 1° C. to 120° C. In some embodiments, the methods, devices and systems are operated in AC frequency ranges of from about 3 to about 15 kHz. In some embodiments, the methods, devices, and systems are operated at voltages of from 5-25 volts pk-pk. In some embodiments, the methods, devices and systems are operated at voltages of from about 1 to about 50 volts/cm. In some embodiments, the methods, devices and systems are operated at DC voltages of from about 1 to about 5 volts. In some embodiments, the methods, devices and systems are operated at a flow rate of from about 10 microliters to about 500 microliters per minute. In some embodiments, the methods, devices and systems are operated in temperature ranges of from about 20° C. to about 60° C. In some embodiments, the methods, devices and systems are operated in AC frequency ranges of from 1,000 Hz to 10 MHz. In some embodiments, the methods, devices and systems are operated in AC frequency ranges of from 1,000 Hz to 1 MHz. In some embodiments, the methods, devices and systems are operated in AC frequency ranges of from 1,000 Hz to 100 kHz. In some embodiments, the methods, devices and systems are operated in AC frequency ranges of from 1,000 Hz to 10 kHz. In some embodiments, the methods, devices and systems are operated in AC frequency ranges of from 10 kHz to 100 kHz. In some embodiments, the methods, devices and systems are operated in AC frequency ranges of from 100 kHz to 1 MHz. In some embodiments, the methods, devices and systems are operated at voltages from approximately 1 volt to 1500 volts pk-pk. In some embodiments, the methods, devices and systems are operated at voltages from approximately 1 volt to 1500 volts pk-pk. In some embodiments, the methods, devices and systems are operated at voltages from approximately 1 volt to 1000 volts pk-pk. In some embodiments, the methods, devices and systems are operated at voltages from approximately 1 volt to 500 volts pk-pk. In some embodiments, the methods, devices and systems are operated at voltages from approximately 1 volt to 250 volts pk-pk. In some embodiments, the methods, devices and systems are operated at voltages from approximately 1 volt to 100 volts pk-pk. In some embodiments, the methods, devices and systems are operated at voltages from approximately 1 volt to 50 volts pk-pk. In some embodiments, the methods, devices and systems are operated at DC voltages from 1 volt to 1000 volts. In some embodiments, the methods, devices and systems are operated at DC voltages from 1 volt to 500 volts. In some embodiments, the methods, devices and systems are operated at DC voltages from 1 volt to 250 volts. In some embodiments, the methods, devices and systems are operated at DC voltages from 1 volt to 100 volts. In some embodiments, the methods, devices and systems are operated at DC voltages from 1 volt to 50 volts. In some embodiments, the methods, devices, and systems are operated at flow rates of from 10 microliters per minute to 1 ml per minute. In some embodiments, the methods, devices, and systems are operated at flow rates of from 10 microliters per minute to 500 microliters per minute. In some embodiments, the methods, devices, and systems are operated at flow rates of from 10 microliters per minute to 250 microliters per minute. In some embodiments, the methods, devices, and systems are operated at flow rates of from 10 microliters per minute to 100 microliters per minute. In some embodiments, the methods, devices, and systems are operated in temperature ranges from 1° C. to 100° C. In some embodiments, the methods, devices, and systems are operated in temperature ranges from 20° C. to 95° C. In some embodiments, the methods, devices, and systems are operated in temperature ranges from 25° C. to 100° C. In some embodiments, the methods, devices, and systems are operated at room temperature.

In some embodiments, the controller independently controls each of the electrodes. In some embodiments, the controller is externally connected to the device such as by a socket and plug connection, or is integrated with the device housing.

Also described herein are scaled sectioned (x-y dimensional) arrays of robust electrodes and strategically placed (x-y-z dimensional) arrangements of auxiliary electrodes that combine DEP, electrophoretic, and fluidic forces, and use thereof. In some embodiments, clinically relevant volumes of blood, serum, plasma, or other samples are more directly analyzed under higher ionic strength and/or conductance conditions. Described herein is the overlaying of robust electrode structures (e.g. platinum, palladium, gold, etc.) with one or more porous layers of materials (natural or synthetic porous hydrogels, membranes, controlled nanopore materials, and thin dielectric layered materials) to reduce the effects of any electrochemistry (electrolysis) reactions, heating, and chaotic fluid movement that may occur on or near the electrodes, and still allow the effective separation of cells, bacteria, virus, nanoparticles, DNA, and other biomolecules to be carried out. In some embodiments, in addition to using AC frequency cross-over points to achieve higher resolution separations, on-device (on-array) DC microelectrophoresis is used for secondary separations. For example, the separation of DNA nanoparticulates (20-50 kb), high molecular weight DNA (5-20 kb), intermediate molecular weight DNA (1-5 kb), and lower molecular weight DNA (0.1-1 kb) fragments may be accomplished through DC microelectrophoresis on the array. In some embodiments, the device is sub-sectioned, optionally for purposes of concurrent separations of different blood cells, bacteria and virus, and DNA carried out simultaneously on such a device.

In some embodiments, the device comprises a housing and a heater or thermal source and/or a reservoir comprising a protein degradation agent. In some embodiments, the heater or thermal source is capable of increasing the temperature of the fluid to a desired temperature (e.g., to a temperature suitable for degrading proteins, about 30° C., 40° C., 50° C., 60° C., 70° C., or the like). In some embodiments, the heater or thermal source is suitable for operation as a PCR thermocycler. IN other embodiments, the heater or thermal source is used to maintain a constant temperature (isothermal conditions). In some embodiments, the protein degradation agent is a protease. In other embodiments, the protein degradation agent is Proteinase K and the heater or thermal source is used to inactivate the protein degradation agent.

In some embodiments, the device also comprises a plurality of alternating current (AC) electrodes within the housing, the AC electrodes capable of being configured to be selectively energized to establish dielectrophoretic (DEP) high field and dielectrophoretic (DEP) low field regions, whereby AC electrokinetic effects provide for concentration of cells in low field regions of the device. In some embodiments, the electrodes are selectively energized to provide the first AC electrokinetic field region and subsequently or continuously selectively energized to provide the second AC electrokinetic field region. For example, further description of the electrodes and the concentration of cells in DEP fields is found in PCT patent publication WO 2009/146143 A2, which is incorporated herein for such disclosure.

In some embodiments, the device comprises a second reservoir comprising an eluant. The eluant is any fluid suitable for eluting the isolated nucleic acid from the device. In some instances the eluant is water or a buffer. In some instances, the eluant comprises reagents required for a DNA sequencing method.

Also provided herein are systems and devices comprising a plurality of alternating current (AC) electrodes, the AC electrodes configured to be selectively energized to establish dielectrophoretic (DEP) high field and dielectrophoretic (DEP) low field regions. In some instances, AC electrokinetic effects provide for concentration of cells in low field regions and/or concentration (or collection or isolation) of molecules (e.g., macromolecules, such as nucleic acid) in high field regions of the DEP field.

Also provided herein are systems and devices comprising a plurality of direct current (DC) electrodes. In some embodiments, the plurality of DC electrodes comprises at least two rectangular electrodes, spread throughout the array. In some embodiments, the electrodes are located at the edges of the array. In some embodiments, DC electrodes are interspersed between AC electrodes.

In some embodiments, a system or device described herein comprises a means for manipulating nucleic acid. In some embodiments, a system or device described herein includes a means of performing enzymatic reactions. In other embodiments, a system or device described herein includes a means of performing polymerase chain reaction, isothermal amplification, ligation reactions, restriction analysis, nucleic acid cloning, transcription or translation assays, or other enzymatic-based molecular biology assay.

In some embodiments, a system or device described herein comprises a nucleic acid sequencer. The sequencer is optionally any suitable DNA sequencing device including but not limited to a Sanger sequencer, pyro-sequencer, ion semiconductor sequencer, polony sequencer, sequencing by ligation device, DNA nanoball sequencing device, sequencing by ligation device, or single molecule sequencing device.

In some embodiments, a system or device described herein is capable of maintaining a constant temperature. In some embodiments, a system or device described herein is capable of cooling the array or chamber. In some embodiments, a system or device described herein is capable of heating the array or chamber. In some embodiments, a system or device described herein comprises a thermocycler. In some embodiments, the devices disclosed herein comprises a localized temperature control element. In some embodiments, the devices disclosed herein are capable of both sensing and controlling temperature.

In some embodiments, the devices further comprise heating or thermal elements. In some embodiments, a heating or thermal element is localized underneath an electrode. In some embodiments, the heating or thermal elements comprise a metal. In some embodiments, the heating or thermal elements comprise tantalum, aluminum, tungsten, or a combination thereof. Generally, the temperature achieved by a heating or thermal element is proportional to the current running through it. In some embodiments, the devices disclosed herein comprise localized cooling elements. In some embodiments, heat resistant elements are placed directly under the exposed electrode array. In some embodiments, the devices disclosed herein are capable of achieving and maintaining a temperature between about 20° C. and about 120° C. In some embodiments, the devices disclosed herein are capable of achieving and maintaining a temperature between about 30° C. and about 100° C. In other embodiments, the devices disclosed herein are capable of achieving and maintaining a temperature between about 20° C. and about 95° C. In some embodiments, the devices disclosed herein are capable of achieving and maintaining a temperature between about 25° C. and about 90° C., between about 25° C. and about 85° C., between about 25° C. and about 75° C., between about 25° C. and about 65° C. or between about 25° C. and about 55° C. In some embodiments, the devices disclosed herein are capable of achieving and maintaining a temperature of about 20° C., about 30° C., about 40° C., about 50° C., about 60° C., about 70° C., about 80° C., about 90° C., about 100° C., about 110° C. or about 120° C.

Electrodes

The plurality of alternating current electrodes are optionally configured in any manner suitable for the separation processes described herein. For example, further description of the system or device including electrodes and/or concentration of cells in DEP fields is found in PCT patent publication WO 2009/146143, which is incorporated herein for such disclosure.

In some embodiments, the electrodes disclosed herein can comprise any suitable metal. In some embodiments, the electrodes can include but are not limited to: aluminum, copper, carbon, iron, silver, gold, palladium, platinum, iridium, platinum iridium alloy, ruthenium, rhodium, osmium, tantalum, titanium, tungsten, polysilicon, and indium tin oxide, or combinations thereof, as well as silicide materials such as platinum silicide, titanium silicide, gold silicide, or tungsten silicide. In some embodiments, the electrodes can comprise a conductive ink capable of being screen-printed.

In some embodiments, the edge to edge (E2E) to diameter ratio of an electrode is about 0.5 mm to about 5 mm. In some embodiments, the E2E to diameter ratio is about 1 mm to about 4 mm. In some embodiments, the E2E to diameter ratio is about 1 mm to about 3 mm. In some embodiments, the E2E to diameter ratio is about 1 mm to about 2 mm. In some embodiments, the E2E to diameter ratio is about 2 mm to about 5 mm. In some embodiments, the E2E to diameter ratio is about 1 mm. In some embodiments, the E2E to diameter ratio is about 2 mm. In some embodiments, the E2E to diameter ratio is about 3 mm. In some embodiments, the E2E to diameter ratio is about 4 mm. In some embodiments, the E2E to diameter ratio is about 5 mm.

In some embodiments, the electrodes disclosed herein are dry-etched. In some embodiments, the electrodes are wet etched. In some embodiments, the electrodes undergo a combination of dry etching and wet etching.

In some embodiments, each electrode is individually site-controlled.

In some embodiments, an array of electrodes is controlled as a unit.

In some embodiments, a passivation layer is employed. In some embodiments, a passivation layer can be formed from any suitable material known in the art. In some embodiments, the passivation layer comprises silicon nitride. In some embodiments, the passivation layer comprises silicon dioxide. In some embodiments, the passivation layer has a relative electrical permittivity of from about 2.0 to about 8.0. In some embodiments, the passivation layer has a relative electrical permittivity of from about 3.0 to about 8.0, about 4.0 to about 8.0 or about 5.0 to about 8.0. In some embodiments, the passivation layer has a relative electrical permittivity of about 2.0 to about 4.0. In some embodiments, the passivation layer has a relative electrical permittivity of from about 2.0 to about 3.0. In some embodiments, the passivation layer has a relative electrical permittivity of about 2.0, about 2.5, about 3.0, about 3.5 or about 4.0.

In some embodiments, the passivation layer is between about 0.1 microns and about 10 microns in thickness. In some embodiments, the passivation layer is between about 0.5 microns and 8 microns in thickness. In some embodiments, the passivation layer is between about 1.0 micron and 5 microns in thickness. In some embodiments, the passivation layer is between about 1.0 micron and 4 microns in thickness. In some embodiments, the passivation layer is between about 1.0 micron and 3 microns in thickness. In some embodiments, the passivation layer is between about 0.25 microns and 2 microns in thickness. In some embodiments, the passivation layer is between about 0.25 microns and 1 micron in thickness.

In some embodiments, the passivation layer is comprised of any suitable insulative low k dielectric material, including but not limited to silicon nitride or silicon dioxide. In some embodiments, the passivation layer is chosen from the group consisting of polyamids, carbon, doped silicon nitride, carbon doped silicon dioxide, fluorine doped silicon nitride, fluorine doped silicon dioxide, porous silicon dioxide, or any combinations thereof. In some embodiments, the passivation layer can comprise a dielectric ink capable of being screen-printed.

Electrode Geometry

In some embodiments, the electrodes disclosed herein can be arranged in any manner suitable for practicing the methods disclosed herein.

In some embodiments, the electrodes are in a dot configuration, e.g. the electrodes comprises a generally circular or round configuration. In some embodiments, the angle of orientation between dots is from about 25° to about 60°. In some embodiments, the angle of orientation between dots is from about 30° to about 55°. In some embodiments, the angle of orientation between dots is from about 30° to about 50°. In some embodiments, the angle of orientation between dots is from about 35° to about 45°. In some embodiments, the angle of orientation between dots is about 25°. In some embodiments, the angle of orientation between dots is about 30°. In some embodiments, the angle of orientation between dots is about 35°. In some embodiments, the angle of orientation between dots is about 40°. In some embodiments, the angle of orientation between dots is about 45°. In some embodiments, the angle of orientation between dots is about 50°. In some embodiments, the angle of orientation between dots is about 55°. In some embodiments, the angle of orientation between dots is about 60°.

In some embodiments, the electrodes are in a substantially elongated configuration.

Figure 8:
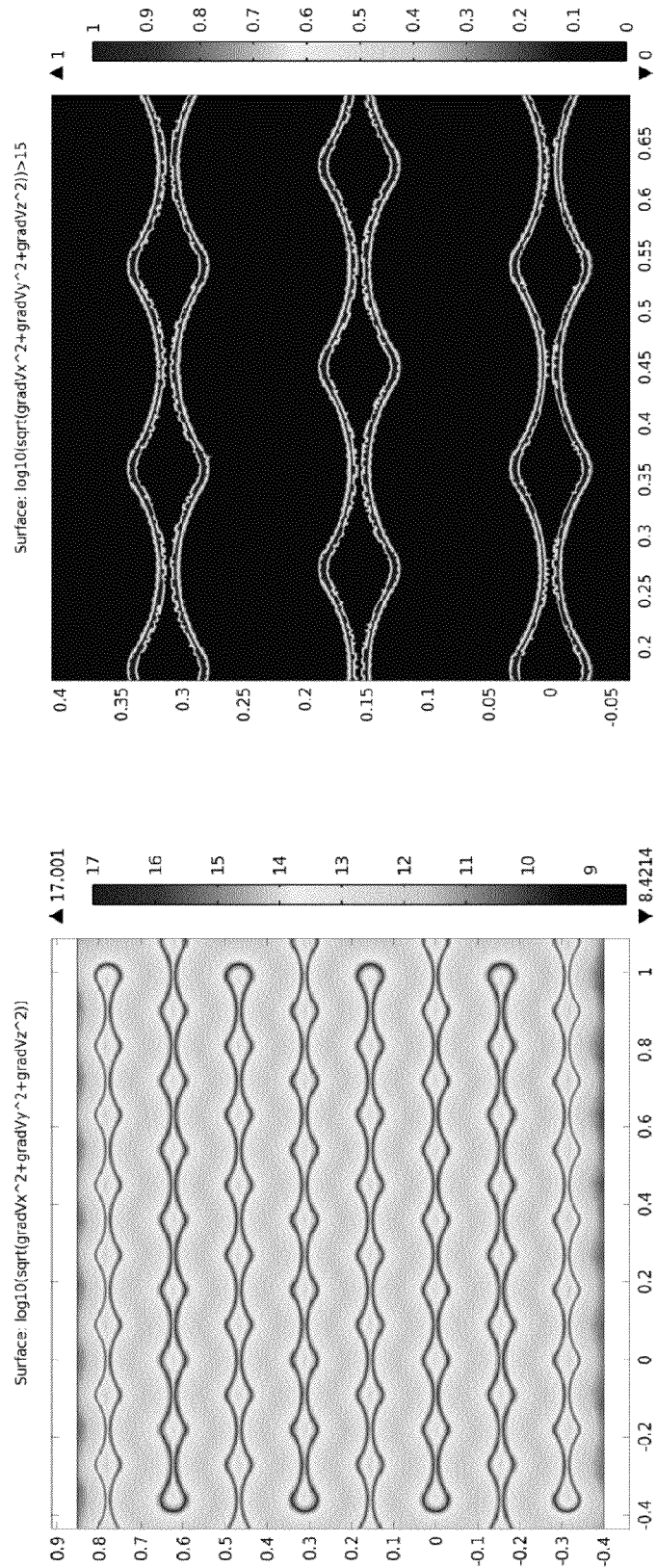
FIG. 8 exemplifies a wavy electrode configuration, as disclosed herein. The edge to edge distance between electrodes is generally equidistant throughout. A wavy electrode configuration maximizes electrode surface area while maintaining alternating non-uniform electric field to induce ACEK gradient to enable DEP, ACEO, ACET, and other ACEK forces.
Figure 9:
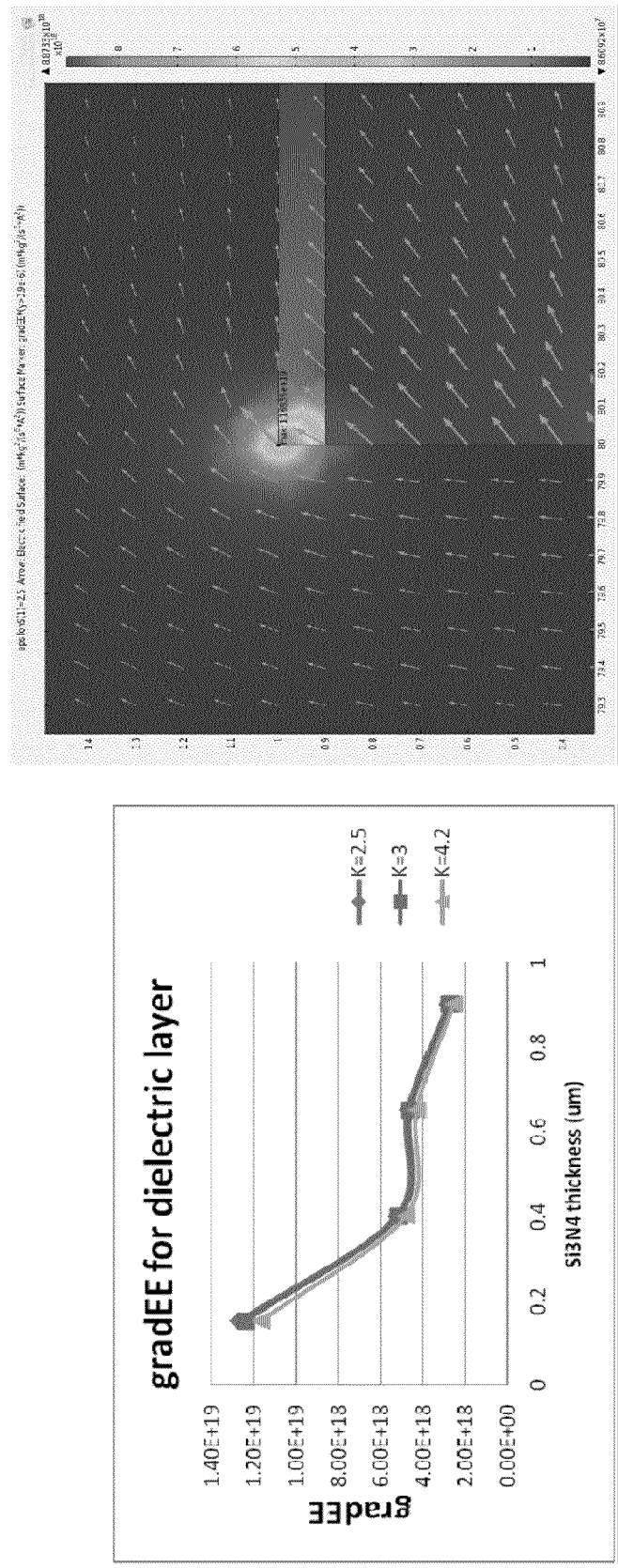
FIG. 9 exemplifies how the E-field gradient at a dielectric layer corner based on silicon nitride thickness. Lower K and lower thickness resulted in higher E-field gradient (bending) at a dielectric layer corner.

In some embodiments, the electrodes are in a configuration resembling wavy or nonlinear lines. In some embodiments, the array of electrodes is in a wavy or nonlinear line configuration, wherein the configuration comprises a repeating unit comprising the shape of a pair of dots connected by a linker, wherein the dots and linker define the boundaries of the electrode, wherein the linker tapers inward towards or at the midpoint between the pair of dots, wherein the diameters of the dots are the widest points along the length of the repeating unit, wherein the edge to edge distance between a parallel set of repeating units is equidistant, or roughly equidistant. In some embodiments, the electrodes are strips resembling wavy lines, as depicted in FIG. 8. In some embodiments, the edge to edge distance between the electrodes is equidistant, or roughly equidistant throughout the wavy line configuration.

In some embodiments, the use of wavy line electrodes, as disclosed herein, lead to an enhanced DEP field gradient.

In some embodiments, the electrodes disclosed herein are in a planar configuration. In some embodiments, the electrodes disclosed herein are in a non-planar configuration.

In some embodiments, the devices disclosed herein surface selectively captures biomolecules on its surface. For example, the devices disclosed herein may capture biomolecules, such as nucleic acids, by, for example, a. nucleic acid hybridization; b. antibody-antigen interactions; c. biotin-avidin interactions; d. ionic or electrostatic interactions; or e. any combination thereof. The devices disclosed herein, therefore, may incorporate a functionalized surface which includes capture molecules, such as complementary nucleic acid probes, antibodies or other protein captures capable of capturing biomolecules (such as nucleic acids), biotin or other anchoring captures capable of capturing complementary target molecules such as avidin, capture molecules capable of capturing biomolecules (such as nucleic acids) by ionic or electrostatic interactions, or any combination thereof.

In some embodiments, the surface is functionalized to minimize and/or inhibit nonspecific binding interactions by: a. polymers (e.g., polyethylene glycol PEG); b. ionic or electrostatic interactions; c. surfactants; or d. any combination thereof. In some embodiments, the methods disclosed herein include use of additives which reduce non-specific binding interactions by interfering in such interactions, such as Tween 20 and the like, bovine serum albumin, nonspecific immunoglobulins, etc.

In some embodiments, the device comprises a plurality of microelectrode devices oriented (a) flat side by side, (b) facing vertically, or (c) facing horizontally. In other embodiments, the electrodes are in a sandwiched configuration, e.g. stacked on top of each other in a vertical format.

Hydrogels

Overlaying electrode structures with one or more layers of materials can reduce the deleterious electrochemistry effects, including but not limited to electrolysis reactions, heating, and chaotic fluid movement that may occur on or near the electrodes, and still allow the effective separation of cells, bacteria, virus, nanoparticles, DNA, and other biomolecules to be carried out. In some embodiments, the materials layered over the electrode structures may be one or more porous layers. In other embodiments, the one or more porous layers is a polymer layer. In other embodiments, the one or more porous layers is a hydrogel.

In general, the hydrogel should have sufficient mechanical strength and be relatively chemically inert such that it will be able to endure the electrochemical effects at the electrode surface without disconfiguration or decomposition. In general, the hydrogel is sufficiently permeable to small aqueous ions, but keeps biomolecules away from the electrode surface.

In some embodiments, the hydrogel is a single layer, or coating.

In some embodiments, the hydrogel comprises a gradient of porosity, wherein the bottom of the hydrogel layer has greater porosity than the top of the hydrogel layer.

In some embodiments, the hydrogel comprises multiple layers or coatings. In some embodiments, the hydrogel comprises two coats. In some embodiments, the hydrogel comprises three coats. In some embodiments, the bottom (first) coating has greater porosity than subsequent coatings. In some embodiments, the top coat is has less porosity than the first coating. In some embodiments, the top coat has a mean pore diameter that functions as a size cut-off for particles of greater than 100 picometers in diameter.

In some embodiments, the hydrogel has a conductivity from about 0.001 S/m to about 10 S/m. In some embodiments, the hydrogel has a conductivity from about 0.01 S/m to about 10 S/m. In some embodiments, the hydrogel has a conductivity from about 0.1 S/m to about 10 S/m. In some embodiments, the hydrogel has a conductivity from about 1.0 S/m to about 10 S/m. In some embodiments, the hydrogel has a conductivity from about 0.01 S/m to about 5 S/m. In some embodiments, the hydrogel has a conductivity from about 0.01 S/m to about 4 S/m. In some embodiments, the hydrogel has a conductivity from about 0.01 S/m to about 3 S/m. In some embodiments, the hydrogel has a conductivity from about 0.01 S/m to about 2 S/m. In some embodiments, the hydrogel has a conductivity from about 0.1 S/m to about 5 S/m. In some embodiments, the hydrogel has a conductivity from about 0.1 S/m to about 4 S/m. In some embodiments, the hydrogel has a conductivity from about 0.1 S/m to about 3 S/m. In some embodiments, the hydrogel has a conductivity from about 0.1 S/m to about 2 S/m. In some embodiments, the hydrogel has a conductivity from about 0.1 S/m to about 1.5 S/m. In some embodiments, the hydrogel has a conductivity from about 0.1 S/m to about 1.0 S/m.

In some embodiments, the hydrogel has a conductivity of about 0.1 S/m. In some embodiments, the hydrogel has a conductivity of about 0.2 S/m. In some embodiments, the hydrogel has a conductivity of about 0.3 S/m. In some embodiments, the hydrogel has a conductivity of about 0.4 S/m. In some embodiments, the hydrogel has a conductivity of about 0.5 S/m. In some embodiments, the hydrogel has a conductivity of about 0.6 S/m. In some embodiments, the hydrogel has a conductivity of about 0.7 S/m. In some embodiments, the hydrogel has a conductivity of about 0.8 S/m. In some embodiments, the hydrogel has a conductivity of about 0.9 S/m. In some embodiments, the hydrogel has a conductivity of about 1.0 S/m.

In some embodiments, the hydrogel has a thickness from about 0.1 microns to about 10 microns. In some embodiments, the hydrogel has a thickness from about 0.1 microns to about 5 microns. In some embodiments, the hydrogel has a thickness from about 0.1 microns to about 4 microns. In some embodiments, the hydrogel has a thickness from about 0.1 microns to about 3 microns. In some embodiments, the hydrogel has a thickness from about 0.1 microns to about 2 microns. In some embodiments, the hydrogel has a thickness from about 1 micron to about 5 microns. In some embodiments, the hydrogel has a thickness from about 1 micron to about 4 microns. In some embodiments, the hydrogel has a thickness from about 1 micron to about 3 microns. In some embodiments, the hydrogel has a thickness from about 1 micron to about 2 microns. In some embodiments, the hydrogel has a thickness from about 0.5 microns to about 1 micron.

In some embodiments, the viscosity of a hydrogel solution prior to spin-coating ranges from about 0.5 cP to about 5 cP. In some embodiments, a single coating of hydrogel solution has a viscosity of between about 0.75 cP and 5 cP prior to spin-coating. In some embodiments, in a multi-coat hydrogel, the first hydrogel solution has a viscosity from about 0.5 cP to about 1.5 cP prior to spin coating. In some embodiments, the second hydrogel solution has a viscosity from about 1 cP to about 3 cP. The viscosity of the hydrogel solution is based on the polymers concentration (0.1%-10%) and polymers molecular weight (10,000 to 300,000) in the solvent and the starting viscosity of the solvent.

In some embodiments, the first hydrogel coating has a thickness between about 0.5 microns and 1 micron. In some embodiments, the first hydrogel coating has a thickness between about 0.5 microns and 0.75 microns. In some embodiments, the first hydrogel coating has a thickness between about 0.75 and 1 micron. In some embodiments, the second hydrogel coating has a thickness between about 0.2 microns and 0.5 microns. In some embodiments, the second hydrogel coating has a thickness between about 0.2 and 0.4 microns. In some embodiments, the second hydrogel coating has a thickness between about 0.2 and 0.3 microns. In some embodiments, the second hydrogel coating has a thickness between about 0.3 and 0.4 microns.

In some embodiments, the hydrogel comprises any suitable synthetic polymer forming a hydrogel. In general, any sufficiently hydrophilic and polymerizable molecule may be utilized in the production of a synthetic polymer hydrogel for use as disclosed herein. Polymerizable moieties in the monomers may include alkenyl moieties including but not limited to substituted or unsubstituted α,β, unsaturated carbonyls wherein the double bond is directly attached to a carbon which is double bonded to an oxygen and single bonded to another oxygen, nitrogen, sulfur, halogen, or carbon; vinyl, wherein the double bond is singly bonded to an oxygen, nitrogen, halogen, phosphorus or sulfur; allyl, wherein the double bond is singly bonded to a carbon which is bonded to an oxygen, nitrogen, halogen, phosphorus or sulfur; homoallyl, wherein the double bond is singly bonded to a carbon which is singly bonded to another carbon which is then singly bonded to an oxygen, nitrogen, halogen, phosphorus or sulfur; alkynyl moieties wherein a triple bond exists between two carbon atoms. In some embodiments, acryloyl or acrylamido monomers such as acrylates, methacrylates, acrylamides, methacrylamides, etc., are useful for formation of hydrogels as disclosed herein. More preferred acrylamido monomers include acrylamides, N-substituted acrylamides, N-substituted methacrylamides, and methacrylamide. In some embodiments, a hydrogel comprises polymers such as epoxide-based polymers, vinyl-based polymers, allyl-based polymers, homoallyl-based polymers, cyclic anhydride-based polymers, ester-based polymers, ether-based polymers, alkylene-glycol based polymers (e.g., polypropylene glycol), and the like.

In some embodiments, the hydrogel comprises polyhydroxyethylmethacrylate (pHEMA), cellulose acetate, cellulose acetate phthalate, cellulose acetate butyrate, or any appropriate acrylamide or vinyl-based polymer, or a derivative thereof.

In some embodiments, the hydrogel is applied by vapor deposition.

In some embodiments, the hydrogel is polymerized via atom-transfer radical-polymerization via (ATRP).

In some embodiments, the hydrogel is polymerized via reversible addition-fragmentation chain-transfer (RAFT) polymerization.

In some embodiments, additives are added to a hydrogel to increase conductivity of the gel. In some embodiments, hydrogel additives are conductive polymers (e.g., PEDOT: PSS), salts (e.g., copper chloride), metals (e.g., gold), plasticizers (e.g., PEG200, PEG 400, or PEG 600), or co-solvents.

In some embodiments, the hydrogel also comprises compounds or materials which help maintain the stability of the DNA hybrids, including, but not limited to histidine, histidine peptides, polyhistidine, lysine, lysine peptides, and other cationic compounds or substances.

Dielectrophoretic Fields

In some embodiments, the methods, devices and systems described herein provide a mechanism to collect, separate, or isolate cells, particles, and/or molecules (such as nucleic acid) from a fluid material (which optionally contains other materials, such as contaminants, residual cellular material, or the like).

In some embodiments, an AC electrokinetic field is generated to collect, separate or isolate biomolecules, such as nucleic acids. In some embodiments, the AC electrokinetic field is a dielectrophoretic field. Accordingly, in some embodiments dielectrophoresis (DEP) is utilized in various steps of the methods described herein.

In some embodiments, the devices and systems described herein are capable of generating DEP fields, and the like. In specific embodiments, DEP is used to concentrate cells and/or nucleic acids (e.g., concurrently or at different times). In certain embodiments, methods described herein further comprise energizing the array of electrodes so as to produce the first, second, and any further optional DEP fields. In some embodiments, the devices and systems described herein are capable of being energized so as to produce the first, second, and any further optional DEP fields.

DEP is a phenomenon in which a force is exerted on a dielectric particle when it is subjected to a non-uniform electric field. Depending on the step of the methods described herein, aspects of the devices and systems described herein, and the like, the dielectric particle in various embodiments herein is a biological cell and/or a molecule, such as a nucleic acid molecule. Different steps of the methods described herein or aspects of the devices or systems described herein may be utilized to isolate and separate different components, such as intact cells or other particular material; further, different field regions of the DEP field may be used in different steps of the methods or aspects of the devices and systems described herein. This dielectrophoretic force does not require the particle to be charged. In some instances, the strength of the force depends on the medium and the specific particles' electrical properties, on the particles' shape and size, as well as on the frequency of the electric field. In some instances, fields of a particular frequency selectivity manipulate particles. In certain aspects described herein, these processes allow for the separation of cells and/or smaller particles (such as molecules, including nucleic acid molecules) from other components (e.g., in a fluid medium) or each other.

In various embodiments provided herein, a method described herein comprises producing a first DEP field region and a second DEP field region with the array. In various embodiments provided herein, a device or system described herein is capable of producing a first DEP field region and a second DEP field region with the array. In some instances, the first and second field regions are part of a single field (e.g., the first and second regions are present at the same time, but are found at different locations within the device and/or upon the array). In some embodiments, the first and second field regions are different fields (e.g. the first region is created by energizing the electrodes at a first time, and the second region is created by energizing the electrodes a second time). In specific aspects, the first DEP field region is suitable for concentrating or isolating cells (e.g., into a low field DEP region). In some embodiments, the second DEP field region is suitable for concentrating smaller particles, such as molecules (e.g., nucleic acid), for example into a high field DEP region. In some instances, a method described herein optionally excludes use of either the first or second DEP field region.

In some embodiments, the first DEP field region is in the same chamber of a device as disclosed herein as the second DEP field region. In some embodiments, the first DEP field region and the second DEP field region occupy the same area of the array of electrodes.

In some embodiments, the first DEP field region is in a separate chamber of a device as disclosed herein, or a separate device entirely, from the second DEP field region.

First DEP Field Region

In some aspects, e.g., high conductance buffers (>100 mS/m), the method described herein comprises applying a fluid comprising cells or other particulate material to a device comprising an array of electrodes, and, thereby, concentrating the cells in a first DEP field region. In some aspects, the devices and systems described herein are capable of applying a fluid comprising cells or other particulate material to the device comprising an array of electrodes, and, thereby, concentrating the cells in a first DEP field region. Subsequent or concurrent second, or optional third and fourth DEP regions, may collect or isolate other fluid components, including biomolecules, such as nucleic acids.

The first DEP field region may be any field region suitable for concentrating cells from a fluid. For this application, the cells are generally concentrated near the array of electrodes. In some embodiments, the first DEP field region is a dielectrophoretic low field region. In some embodiments, the first DEP field region is a dielectrophoretic high field region. In some aspects, e.g. low conductance buffers (<100 mS/m), the method described herein comprises applying a fluid comprising cells to a device comprising an array of electrodes, and, thereby, concentrating the cells or other particulate material in a first DEP field region.

In some aspects, the devices and systems described herein are capable of applying a fluid comprising cells or other particulate material to the device comprising an array of electrodes, and concentrating the cells in a first DEP field region. In various embodiments, the first DEP field region may be any field region suitable for concentrating cells from a fluid. In some embodiments, the cells are concentrated on the array of electrodes. In some embodiments, the cells are captured in a dielectrophoretic high field region. In some embodiments, the cells are captured in a dielectrophoretic low-field region. High versus low field capture is generally dependent on the conductivity of the fluid, wherein generally, the crossover point is between about 300-500 mS/m. In some embodiments, the first DEP field region is a dielectrophoretic low field region performed in fluid conductivity of greater than about 300 mS/m. In some embodiments, the first DEP field region is a dielectrophoretic low field region performed in fluid conductivity of less than about 300 mS/m. In some embodiments, the first DEP field region is a dielectrophoretic high field region performed in fluid conductivity of greater than about 300 mS/m. In some embodiments, the first DEP field region is a dielectrophoretic high field region performed in fluid conductivity of less than about 300 mS/m. In some embodiments, the first DEP field region is a dielectrophoretic low field region performed in fluid conductivity of greater than about 500 mS/m. In some embodiments, the first DEP field region is a dielectrophoretic low field region performed in fluid conductivity of less than about 500 mS/m. In some embodiments, the first DEP field region is a dielectrophoretic high field region performed in fluid conductivity of greater than about 500 mS/m. In some embodiments, the first DEP field region is a dielectrophoretic high field region performed in fluid conductivity of less than about 500 mS/m.

In some embodiments, the first dielectrophoretic field region is produced by an alternating current. The alternating current has any amperage, voltage, frequency, and the like suitable for concentrating cells. In some embodiments, the first dielectrophoretic field region is produced using an alternating current having an amperage of 0.1 micro Amperes-10 Amperes; a voltage of 1-50 Volts peak to peak; and/or a frequency of 1-10,000,000 Hz. In some embodiments, the first DEP field region is produced using an alternating current having a voltage of 5-25 volts peak to peak. In some embodiments, the first DEP field region is produced using an alternating current having a frequency of from 3-15 kHz. In some embodiments, the first DEP field region is produced using an alternating current having an amperage of 1 milliamp to 1 amp. In some embodiments, the first DEP field region is produced using an alternating current having an amperage of 0.1 micro Amperes-1 Ampere. In some embodiments, the first DEP field region is produced using an alternating current having an amperage of 1 micro Amperes-1 Ampere. In some embodiments, the first DEP field region is produced using an alternating current having an amperage of 100 micro Amperes-1 Ampere. In some embodiments, the first DEP field region is produced using an alternating current having an amperage of 500 micro Amperes-500 milli Amperes. In some embodiments, the first DEP field region is produced using an alternating current having a voltage of 1-25 Volts peak to peak. In some embodiments, the first DEP field region is produced using an alternating current having a voltage of 1-10 Volts peak to peak. In some embodiments, the first DEP field region is produced using an alternating current having a voltage of 25-50 Volts peak to peak. In some embodiments, the first DEP field region is produced using a frequency of from 10-1,000,000 Hz. In some embodiments, the first DEP field region is produced using a frequency of from 100-100,000 Hz. In some embodiments, the first DEP field region is produced using a frequency of from 100-10,000 Hz. In some embodiments, the first DEP field region is produced using a frequency of from 10,000-100,000 Hz. In some embodiments, the first DEP field region is produced using a frequency of from 100,000-1,000,000 Hz.

In some embodiments, the first dielectrophoretic field region is produced by a direct current. The direct current has any amperage, voltage, frequency, and the like suitable for concentrating cells. In some embodiments, the first dielectrophoretic field region is produced using a direct current having an amperage of 0.1 micro Amperes-1 Amperes; a voltage of 10 milli Volts-10 Volts; and/or a pulse width of 1 milliseconds-1000 seconds and a pulse frequency of 0.001-1000 Hz. In some embodiments, the first DEP field region is produced using a direct current having an amperage of 1 micro Amperes-1 Amperes. In some embodiments, the first DEP field region is produced using a direct current having an amperage of 100 micro Amperes-500 milli Amperes. In some embodiments, the first DEP field region is produced using a direct current having an amperage of 1 milli Amperes-1 Amperes. In some embodiments, the first DEP field region is produced using a direct current having an amperage of 1 micro Amperes-1 milli Amperes. In some embodiments, the first DEP field region is produced using a direct current having a pulse width of 500 milliseconds-500 seconds. In some embodiments, the first DEP field region is produced using a direct current having a pulse width of 500 milliseconds-100 seconds. In some embodiments, the first DEP field region is produced using a direct current having a pulse width of 1 second-1000 seconds. In some embodiments, the first DEP field region is produced using a direct current having a pulse width of 500 milliseconds-1 second. In some embodiments, the first DEP field region is produced using a pulse frequency of 0.01-1000 Hz. In some embodiments, the first DEP field region is produced using a pulse frequency of 0.1-100 Hz. In some embodiments, the first DEP field region is produced using a pulse frequency of 1-100 Hz. In some embodiments, the first DEP field region is produced using a pulse frequency of 100-1000 Hz.

In some embodiments, the fluid comprises a mixture of cell types. For example, blood comprises red blood cells and white blood cells. Environmental samples comprise many types of cells and other particulate material over a wide range of concentrations. In some embodiments, one cell type (or any number of cell types less than the total number of cell types comprising the sample) is preferentially concentrated in the first DEP field. Without limitation, this embodiment is beneficial for focusing the nucleic acid isolation procedure on a particular environmental contaminant, such as a fecal coliform bacterium, whereby DNA sequencing may be used to identify the source of the contaminant. In another non-limiting example, the first DEP field is operated in a manner that specifically concentrates viruses and not cells (e.g., in a fluid with conductivity of greater than 300 mS/m, viruses concentrate in a DEP high field region, while larger cells will concentrate in a DEP low field region).

In some embodiments, a method, device or system described herein is suitable for isolating or separating specific cell types. In some embodiments, the DEP field of the method, device or system is specifically tuned to allow for the separation or concentration of a specific type of cell into a field region of the DEP field. In some embodiments, a method, device or system described herein provides more than one field region wherein more than one type of cell is isolated or concentrated. In some embodiments, a method, device, or system described herein is tunable so as to allow isolation or concentration of different types of cells within the DEP field regions thereof. In some embodiments, a method provided herein further comprises tuning the DEP field. In some embodiments, a device or system provided herein is capable of having the DEP field tuned. In some instances, such tuning may be in providing a DEP particularly suited for the desired purpose. For example, modifications in the array, the energy, or another parameter are optionally utilized to tune the DEP field. Tuning parameters for finer resolution include electrode diameter, edge to edge distance between electrodes, voltage, frequency, fluid conductivity and hydrogel composition.

In some embodiments, the first DEP field region comprises the entirety of an array of electrodes. In some embodiments, the first DEP field region comprises a portion of an array of electrodes. In some embodiments, the first DEP field region comprises about 90%, about 80%, about 70%, about 60%, about 50%, about 40%, about 30%, about 25%, about 20%, or about 10% of an array of electrodes. In some embodiments, the first DEP field region comprises about a third of an array of electrodes.

Second DEP Field Region

In one aspect, following lysis of the cells (as provided below), the methods described herein involve concentrating the nucleic acid in a second DEP field region. In another aspect, the devices and systems described herein are capable of concentrating the nucleic acid in a second DEP field region. In some embodiments, the second DEP field region is any field region suitable for concentrating nucleic acids. In some embodiments, the nucleic acids are concentrated on the array of electrodes. In some embodiments, the second DEP field region is a dielectrophoretic high field region. The second DEP field region is, optionally, the same as the first DEP field region.

In some embodiments, the second dielectrophoretic field region is produced by an alternating current. In some embodiments, the alternating current has any amperage, voltage, frequency, and the like suitable for concentrating nucleic acids. In some embodiments, the second dielectrophoretic field region is produced using an alternating current having an amperage of 0.1 micro Amperes-10 Amperes; a voltage of 1-50 Volts peak to peak; and/or a frequency of 1-10,000,000 Hz. In some embodiments, the second DEP field region is produced using an alternating current having an amperage of 0.1 micro Amperes-1 Ampere. In some embodiments, the second DEP field region is produced using an alternating current having an amperage of 1 micro Amperes-1 Ampere. In some embodiments, the second DEP field region is produced using an alternating current having an amperage of 100 micro Amperes-1 Ampere. In some embodiments, the second DEP field region is produced using an alternating current having an amperage of 500 micro Amperes-500 milli Amperes. In some embodiments, the second DEP field region is produced using an alternating current having a voltage of 1-25 Volts peak to peak. In some embodiments, the second DEP field region is produced using an alternating current having a voltage of 1-10 Volts peak to peak. In some embodiments, the second DEP field region is produced using an alternating current having a voltage of 25-50 Volts peak to peak. In some embodiments, the second DEP field region is produced using a frequency of from 10-1,000,000 Hz. In some embodiments, the second DEP field region is produced using a frequency of from 100-100,000 Hz. In some embodiments, the second DEP field region is produced using a frequency of from 100-10,000 Hz. In some embodiments, the second DEP field region is produced using a frequency of from 10,000-100,000 Hz. In some embodiments, the second DEP field region is produced using a frequency of from 100,000-1,000,000 Hz.

In some embodiments, the second dielectrophoretic field region is produced by a direct current. In some embodiments, the direct current has any amperage, voltage, frequency, and the like suitable for concentrating nucleic acids. In some embodiments, the second dielectrophoretic field region is produced using a direct current having an amperage of 0.1 micro Amperes-1 Amperes; a voltage of 10 milli Volts-10 Volts; and/or a pulse width of 1 milliseconds-1000 seconds and a pulse frequency of 0.001-1000 Hz. In some embodiments, the second DEP field region is produced using an alternating current having a voltage of 5-25 volts peak to peak. In some embodiments, the second DEP field region is produced using an alternating current having a frequency of from 3-15 kHz. In some embodiments, the second DEP field region is produced using an alternating current having an amperage of 1 milliamp to 1 amp. In some embodiments, the second DEP field region is produced using a direct current having an amperage of 1 micro Amperes-1 Amperes. In some embodiments, the second DEP field region is produced using a direct current having an amperage of 100 micro Amperes-500 milli Amperes. In some embodiments, the second DEP field region is produced using a direct current having an amperage of 1 milli Amperes-1 Amperes. In some embodiments, the second DEP field region is produced using a direct current having an amperage of 1 micro Amperes-1 milli Amperes. In some embodiments, the second DEP field region is produced using a direct current having a pulse width of 500 milliseconds-500 seconds. In some embodiments, the second DEP field region is produced using a direct current having a pulse width of 500 milliseconds-100 seconds. In some embodiments, the second DEP field region is produced using a direct current having a pulse width of 1 second-1000 seconds. In some embodiments, the second DEP field region is produced using a direct current having a pulse width of 500 milliseconds-1 second. In some embodiments, the second DEP field region is produced using a pulse frequency of 0.01-1000 Hz. In some embodiments, the second DEP field region is produced using a pulse frequency of 0.1-100 Hz. In some embodiments, the second DEP field region is produced using a pulse frequency of 1-100 Hz. In some embodiments, the second DEP field region is produced using a pulse frequency of 100-1000 Hz.

In some embodiments, the second DEP field region comprises the entirety of an array of electrodes. In some embodiments, the second DEP field region comprises a portion of an array of electrodes. In some embodiments, the second DEP field region comprises about 90%, about 80%, about 70%, about 60%, about 50%, about 40%, about 30%, about 25%, about 20%, or about 10% of an array of electrodes. In some embodiments, the second DEP field region comprises about a third of an array of electrodes.

Isolating Nucleic Acids

Figure 5:
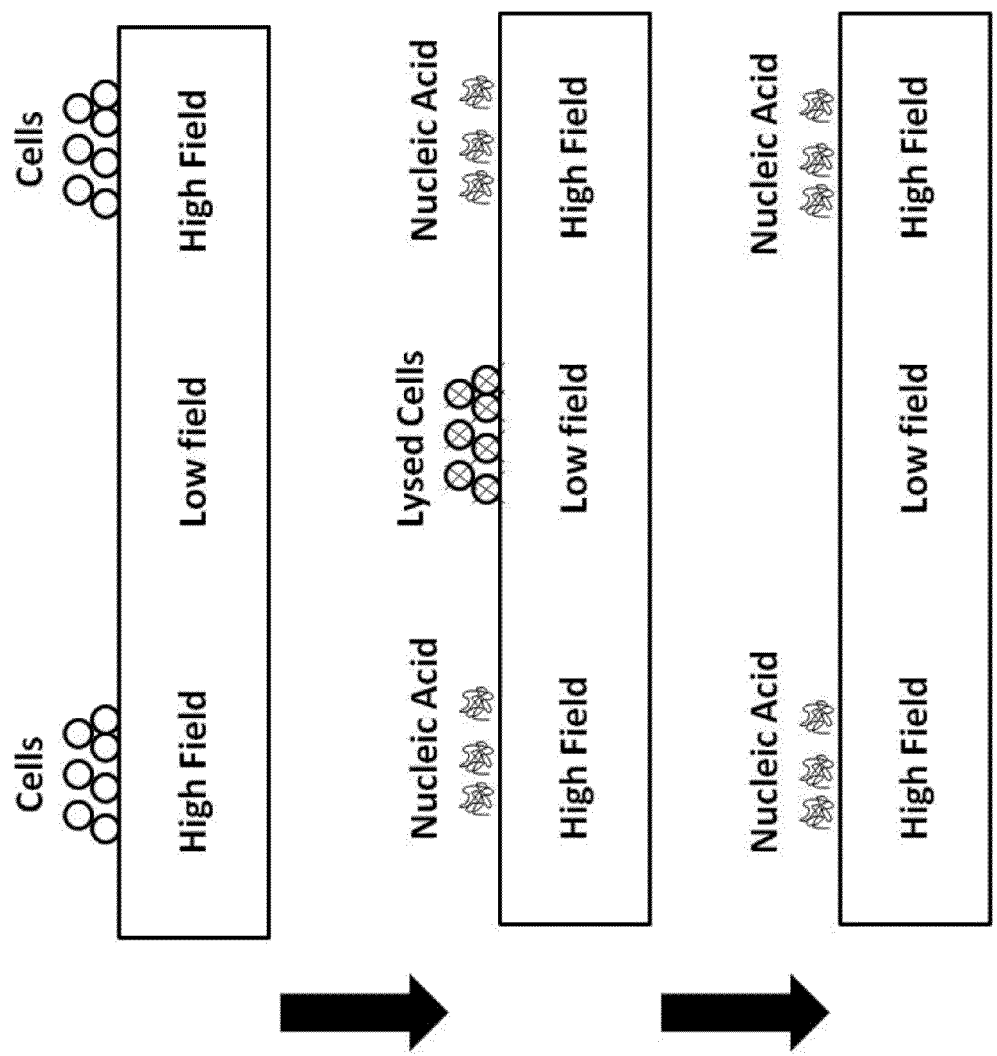
FIG. 5 shows an exemplary method for isolating nucleic acids from cells.

In one aspect, described herein is a method for isolating a nucleic acid from a fluid comprising cells. In some embodiments, the nucleic acids are initially inside the cells. As seen in FIG. 5, the method comprises concentrating the cells near a high field region in some instances. In some embodiments, disclosed herein is method for isolating a nucleic acid from a fluid comprising cells, the method comprising: a. applying the fluid to a device, the device comprising an array of electrodes; b. concentrating a plurality of cells in a first AC electrokinetic (e.g., dielectrophoretic) field region; c. isolating nucleic acid in a second AC electrokinetic (e.g., dielectrophoretic) field region; and d. flushing cells away. In some instances, the cells are lysed in the high field region. Following lysis, the nucleic acids remain in the high field region and/or are concentrated in the high field region. In some instances, residual cellular material is concentrated near the low field region. In some embodiments, the residual material is washed from the device and/or washed from the nucleic acids. In some embodiments, the nucleic acid is concentrated in the second AC electrokinetic field region.

Figure 6:
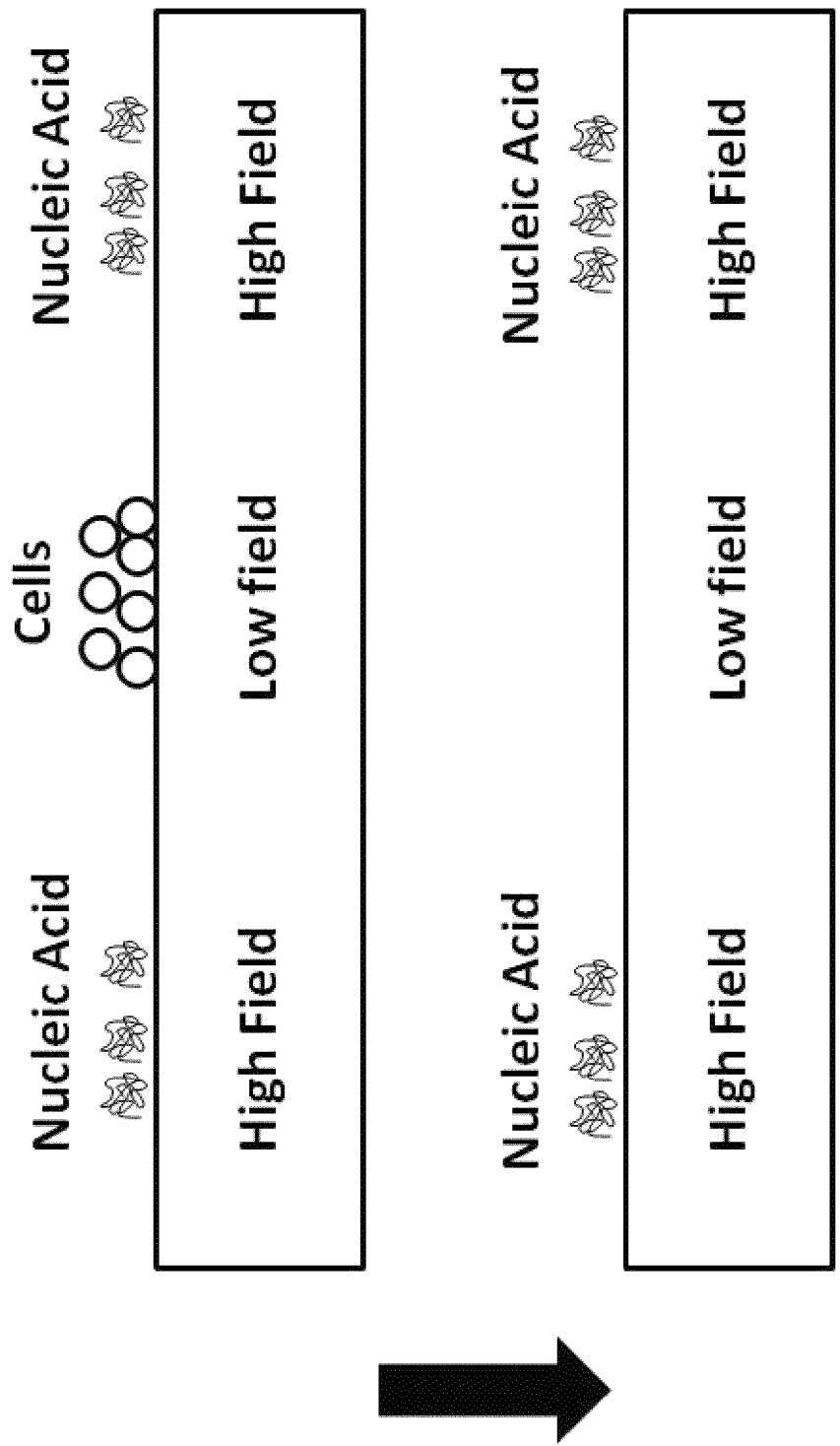
FIG. 6 shows an exemplary method for isolating extracellular nucleic acids from a fluid comprising cells.
Figure 7:
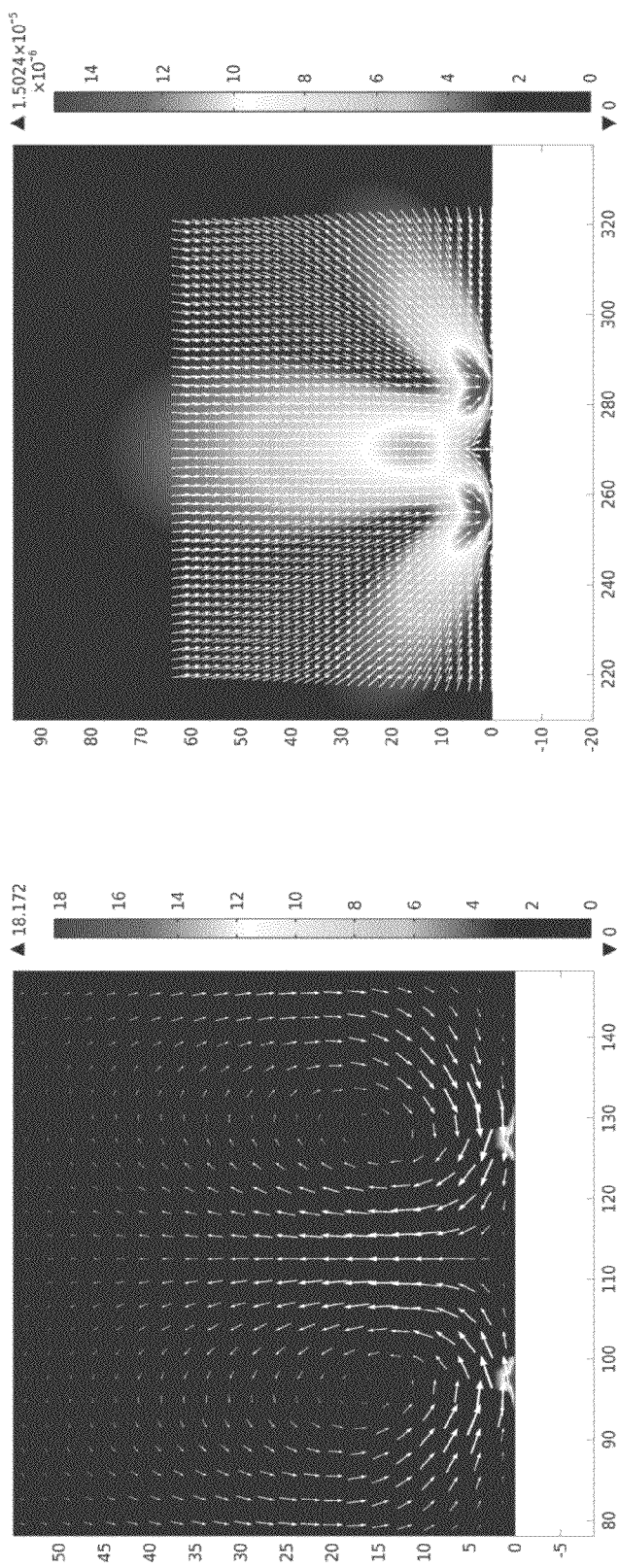
FIG. 7 exemplifies ACEK (AC Electrokinetic) forces that result due to the methods and devices disclosed herein. Using the relationship between forces on particles due to Dielectrophoresis (DEP), AC Electrothermal (ACET) flow and AC Electroosmosis, (ACEO), in some embodiments, size cutoffs are used for nucleic acid isolation and purification. Isolation relies on flow vortices that will brings nucleic acids closer to an electrode edge due to ACET and ACEO depending on fluid conductivity, A DEP trap holds onto particles once they are at the trap site, depending on the effective Stokes radius.

In one aspect, described herein is a method for isolating a nucleic acid from a fluid comprising cells or other particulate material. In some embodiments, the nucleic acids are not inside the cells (e.g., cell-free DNA in fluid). In some embodiments, disclosed herein is a method for isolating a nucleic acid from a fluid comprising cells or other particulate material, the method comprising: a. applying the fluid to a device, the device comprising an array of electrodes; b. concentrating a plurality of cells in a first AC electrokinetic (e.g., dielectrophoretic) field region; c. isolating nucleic acid in a second AC electrokinetic (e.g., dielectrophoretic) field region; and d. flushing cells away. In some embodiments, the method further comprises degrading residual proteins after flushing cells away. FIG. 6 shows an exemplary method for isolating extracellular nucleic acids from a fluid comprising cells. In some embodiments, cells are concentrated on or near a low field region and nucleic acids are concentrated on or near a high field region. In some instances, the cells are washed from the device and/or washed from the nucleic acids.

In one aspect, the methods, systems and devices described herein isolate nucleic acid from a fluid comprising cells or other particulate material. In one aspect, dielectrophoresis is used to concentrate cells. In some embodiments, the fluid is a liquid, optionally water or an aqueous solution or dispersion. In some embodiments, the fluid is any suitable fluid including a bodily fluid. Exemplary bodily fluids include blood, serum, plasma, bile, milk, cerebrospinal fluid, gastric juice, ejaculate, mucus, peritoneal fluid, saliva, sweat, tears, urine, and the like. In some embodiments, nucleic acids are isolated from bodily fluids using the methods, systems or devices described herein as part of a medical therapeutic or diagnostic procedure, device or system. In some embodiments, the fluid is tissues and/or cells solubilized and/or dispersed in a fluid.

For example, the tissue can be a cancerous tumor from which nucleic acid can be isolated using the methods, devices or systems described herein.

In some embodiments, the fluid is an environmental sample. In some embodiments, the environmental sample is assayed or monitored for the presence of a particular nucleic acid sequence indicative of a certain contamination, infestation incidence or the like. The environmental sample can also be used to determine the source of a certain contamination, infestation incidence or the like using the methods, devices or systems described herein. Exemplary environmental samples include municipal wastewater, industrial wastewater, water or fluid used in or produced as a result of various manufacturing processes, lakes, rivers, oceans, aquifers, ground water, storm water, plants or portions of plants, animals or portions of animals, insects, municipal water supplies, and the like.

In some embodiments, the fluid is a food or beverage. The food or beverage can be assayed or monitored for the presence of a particular nucleic acid sequence indicative of a certain contamination, infestation incidence or the like. The food or beverage can also be used to determine the source of a certain contamination, infestation incidence or the like using the methods, devices or systems described herein. In various embodiments, the methods, devices and systems described herein can be used with one or more of bodily fluids, environmental samples, and foods and beverages to monitor public health or respond to adverse public health incidences.

In some embodiments, the fluid is a growth medium. The growth medium can be any medium suitable for culturing cells, for example lysogeny broth (LB) for culturing $E.\ coli$, Ham's tissue culture medium for culturing mammalian cells, and the like. The medium can be a rich medium, minimal medium, selective medium, and the like. In some embodiments, the medium comprises or consists essentially of a plurality of clonal cells. In some embodiments, the medium comprises a mixture of at least two species.

In some embodiments, the fluid is water.

The cells are any cell suitable for isolating nucleic acids from as described herein. In various embodiments, the cells are eukaryotic or prokaryotic. In various embodiments, the cells consist essentially of a plurality of clonal cells or may comprise at least two species and/or at least two strains.

In various embodiments, the cells are pathogen cells, bacteria cells, plant cells, animal cells, insect cells, algae cells, cyanobacterial cells, organelles and/or combinations thereof. As used herein, "cells" include viruses and other intact pathogenic microorganisms. The cells can be microorganisms or cells from multi-cellular organisms. In some instances, the cells originate from a solubilized tissue sample.

In various embodiments, the cells are wild-type or genetically engineered. In some instances, the cells comprise a library of mutant cells. In some embodiments, the cells are randomly mutagenized such as having undergone chemical mutagenesis, radiation mutagenesis (e.g. UV radiation), or a combination thereof. In some embodiments, the cells have been transformed with a library of mutant nucleic acid molecules.

In some embodiments, the fluid may also comprise other particulate material. Such particulate material may be, for example, inclusion bodies (e.g., ceroids or Mallory bodies), cellular casts (e.g., granular casts, hyaline casts, cellular casts, waxy casts and pseudo casts), Pick's bodies, Lewy bodies, fibrillary tangles, fibril formations, cellular debris and other particulate material. In some embodiments, particulate material is an aggregated protein (e.g., beta-amyloid).

The fluid can have any conductivity including a high or low conductivity. In some embodiments, the conductivity is between about 1 µS/m to about 10 mS/m. In some embodiments, the conductivity is between about 10 µS/m to about 10 mS/m. In other embodiments, the conductivity is between about 50 µS/m to about 10 mS/m. In yet other embodiments, the conductivity is between about 100 µS/m to about 10 mS/m, between about 100 µS/m to about 8 mS/m, between about 100 µS/m to about 6 mS/m, between about 100 µS/m to about 5 mS/m, between about 100 µS/m to about 4 mS/m, between about 100 µS/m to about 3 mS/m, between about 100 µS/m to about 2 mS/m, or between about 100 µS/m to about 1 mS/m.

In some embodiments, the conductivity is about 1 µS/m. In some embodiments, the conductivity is about 10 µS/m. In some embodiments, the conductivity is about 100 µS/m. In some embodiments, the conductivity is about 1 mS/m. In other embodiments, the conductivity is about 2 mS/m. In some embodiments, the conductivity is about 3 mS/m. In yet other embodiments, the conductivity is about 4 mS/m. In some embodiments, the conductivity is about 5 mS/m. In some embodiments, the conductivity is about 10 mS/m. In still other embodiments, the conductivity is about 100 mS/m. In some embodiments, the conductivity is about 1 S/m. In other embodiments, the conductivity is about 10 S/m.

In some embodiments, the conductivity is at least 1 µS/m. In yet other embodiments, the conductivity is at least 10 µS/m. In some embodiments, the conductivity is at least 100 µS/m. In some embodiments, the conductivity is at least 1 mS/m. In additional embodiments, the conductivity is at least 10 mS/m. In yet other embodiments, the conductivity is at least 100 mS/m. In some embodiments, the conductivity is at least 1 S/m. In some embodiments, the conductivity is at least 10 S/m. In some embodiments, the conductivity is at most 1 µS/m. In some embodiments, the conductivity is at most 10 µS/m. In other embodiments, the conductivity is at most 100 µS/m. In some embodiments, the conductivity is at most 1 mS/m. In some embodiments, the conductivity is at most 10 mS/m. In some embodiments, the conductivity is at most 100 mS/m. In yet other embodiments, the conductivity is at most 1 S/m. In some embodiments, the conductivity is at most 10 S/m.

In some embodiments, the fluid is a small volume of liquid including less than 10 ml. In some embodiments, the fluid is less than 8 ml. In some embodiments, the fluid is less than 5 ml. In some embodiments, the fluid is less than 2 ml. In some embodiments, the fluid is less than 1 ml. In some embodiments, the fluid is less than 500 µl. In some embodiments, the fluid is less than 200 µl. In some embodiments, the fluid is less than 100 µl. In some embodiments, the fluid is less than 50 µl. In some embodiments, the fluid is less than 10 µl. In some embodiments, the fluid is less than 5 µl. In some embodiments, the fluid is less than 1 µl.

In some embodiments, the quantity of fluid applied to the device or used in the method comprises less than about 100,000,000 cells. In some embodiments, the fluid comprises less than about 10,000,000 cells. In some embodiments, the fluid comprises less than about 1,000,000 cells. In some embodiments, the fluid comprises less than about 100,000 cells. In some embodiments, the fluid comprises less than about 10,000 cells. In some embodiments, the fluid comprises less than about 1,000 cells.

In some embodiments, isolation of nucleic acid from a fluid comprising cells or other particulate material with the devices, systems and methods described herein takes less than about 30 minutes, less than about 20 minutes, less than about 15 minutes, less than about 10 minutes, less than about 5 minutes or less than about 1 minute. In other embodiments, isolation of nucleic acid from a fluid comprising cells or other particulate material with the devices, systems and methods described herein takes not more than 30 minutes, not more than about 20 minutes, not more than about 15 minutes, not more than about 10 minutes, not more than about 5 minutes, not more than about 2 minutes or not more than about 1 minute. In additional embodiments, isolation of nucleic acid from a fluid comprising cells or other particulate material with the devices, systems and methods described herein takes less than about 15 minutes, preferably less than about 10 minutes or less than about 5 minutes.

In some instances, extra-cellular DNA or other nucleic acid (outside cells) is isolated from a fluid comprising cells of other particulate material. In some embodiments, the fluid comprises cells. In some embodiments, the fluid does not comprise cells.

Cell Lysis

In one aspect, following concentrating the cells in a first dielectrophoretic field region, the method involves freeing nucleic acids from the cells. In another aspect, the devices and systems described herein are capable of freeing nucleic acids from the cells. In some embodiments, the nucleic acids are freed from the cells in the first DEP field region.

In some embodiments, the methods described herein free nucleic acids from a plurality of cells by lysing the cells. In some embodiments, the devices and systems described herein are capable of freeing nucleic acids from a plurality of cells by lysing the cells. One method of cell lysis involves applying a direct current to the cells after isolation of the cells on the array. The direct current has any suitable amperage, voltage, and the like suitable for lysing cells. In some embodiments, the current has a voltage of about 1 Volt to about 500 Volts. In some embodiments, the current has a voltage of about 10 Volts to about 500 Volts. In other embodiments, the current has a voltage of about 10 Volts to about 250 Volts. In still other embodiments, the current has a voltage of about 50 Volts to about 150 Volts. Voltage is generally the driver of cell lysis, as high electric fields result in failed membrane integrity.

In some embodiments, the direct current used for lysis comprises one or more pulses having any duration, frequency, and the like suitable for lysing cells. In some embodiments, a voltage of about 100 volts is applied for about 1 millisecond to lyse cells. In some embodiments, the voltage of about 100 volts is applied 2 or 3 times over the source of a second.

In some embodiments, the frequency of the direct current depends on volts/cm, pulse width, and the fluid conductivity. In some embodiments, the pulse has a frequency of about 0.001 to about 1000 Hz. In some embodiments, the pulse has a frequency from about 10 to about 200 Hz. In other embodiments, the pulse has a frequency of about 0.01 Hz-1000 Hz. In still other embodiments, the pulse has a frequency of about 0.1 Hz-1000 Hz, about 1 Hz-1000 Hz, about 1 Hz-500 Hz, about 1 Hz-400 Hz, about 1 Hz-300 Hz, or about 1 Hz-about 250 Hz. In some embodiments, the pulse has a frequency of about 0.1 Hz. In other embodiments, the pulse has a frequency of about 1 Hz. In still other embodiments, the pulse has a frequency of about 5 Hz, about 10 Hz, about 50 Hz, about 100 Hz, about 200 Hz, about 300 Hz, about 400 Hz, about 500 Hz, about 600 Hz, about 700 Hz, about 800 Hz, about 900 Hz or about 1000 Hz.

In other embodiments, the pulse has a duration of about 1 millisecond (ms)-1000 seconds (s). In some embodiments, the pulse has a duration of about 10 ms-1000 s. In still other embodiments, the pulse has a duration of about 100 ms-1000 s, about 1 s-1000 s, about 1 s-500 s, about 1 s-250 s or about 1 s-150 s. In some embodiments, the pulse has a duration of about 1 ms, about 10 ms, about 100 ms, about 1 s, about 2 s, about 3 s, about 4 s, about 5 s, about 6 s, about 7 s, about 8 s, about 9 s, about 10 s, about 20 s, about 50 s, about 100 s, about 200 s, about 300 s, about 500 s or about 1000 s. In some embodiments, the pulse has a frequency of 0.2 to 200 Hz with duty cycles from 10-50%.

In some embodiments, the direct current is applied once, or as multiple pulses. Any suitable number of pulses may be applied including about 1-20 pulses. There is any suitable amount of time between pulses including about 1 millisecond-1000 seconds. In some embodiments, the pulse duration is 0.01 to 10 seconds.

In some embodiments, the cells are lysed using other methods in combination with a direct current applied to the isolated cells. In yet other embodiments, the cells are lysed without use of direct current. In various aspects, the devices and systems are capable of lysing cells with direct current in combination with other means, or may be capable of lysing cells without the use of direct current. Any method of cell lysis known to those skilled in the art may be suitable including, but not limited to application of a chemical lysing agent (e.g., an acid), an enzymatic lysing agent, heat, pressure, shear force, sonic energy, osmotic shock, or combinations thereof. Lysozyme is an example of an enzymatic-lysing agent.

Removal of Residual Material

In some embodiments, following concentration of the nucleic acids in the second DEP field region, the method includes optionally flushing residual material from the nucleic acid. In some embodiments, the devices or systems described herein are capable of optionally and/or comprising a reservoir comprising a fluid suitable for flushing residual material from the nucleic acid. In some embodiments, the nucleic acid is held near the array of electrodes, such as in the second DEP field region, by continuing to energize the electrodes. "Residual material" is anything originally present in the fluid, originally present in the cells, added during the procedure, created through any step of the process including but not limited to lysis of the cells (i.e. residual cellular material), and the like. For example, residual material includes non-lysed cells, cell wall fragments, proteins, lipids, carbohydrates, minerals, salts, buffers, plasma, and undesired nucleic acids. In some embodiments, the lysed cellular material comprises residual protein freed from the plurality of cells upon lysis. It is possible that not all of the nucleic acid will be concentrated in the second DEP field. In some embodiments, a certain amount of nucleic acid is flushed with the residual material.

In some embodiments, the residual material is flushed in any suitable fluid, for example in water, TBE buffer, or the like. In some embodiments, the residual material is flushed with any suitable volume of fluid, flushed for any suitable period of time, flushed with more than one fluid, or any other variation. In some embodiments, the method of flushing residual material is related to the desired level of isolation of the nucleic acid, with higher purity nucleic acid requiring more stringent flushing and/or washing. In other embodiments, the method of flushing residual material is related to the particular starting material and its composition. In some instances, a starting material that is high in lipid requires a flushing procedure that involves a hydrophobic fluid suitable for solubilizing lipids.

In some embodiments, the method includes degrading residual material including residual protein. In some embodiments, the devices or systems are capable of degrading residual material including residual protein. For example, proteins are degraded by one or more of chemical degradation (e.g. acid hydrolysis) and enzymatic degradation. In some embodiments, the enzymatic degradation agent is a protease.

In other embodiments, the protein degradation agent is Proteinase K. The optional step of degradation of residual material is performed for any suitable time, temperature, and the like. In some embodiments, the degraded residual material (including degraded proteins) is flushed from the nucleic acid.

In some embodiments, the agent used to degrade the residual material is inactivated or degraded. In some embodiments, the devices or systems are capable of degrading or inactivating the agent used to degrade the residual material. In some embodiments, an enzyme used to degrade the residual material is inactivated by heat (e.g., 50 to 95° C. for 5-15 minutes). For example, enzymes including proteases, (for example, Proteinase K) are degraded and/or inactivated using heat (typically, 15 minutes, 70° C.). In some embodiments wherein the residual proteins are degraded by an enzyme, the method further comprises inactivating the degrading enzyme (e.g., Proteinase K) following degradation of the proteins. In some embodiments, heat is provided by a heating module in the device (temperature range, e.g., from 30 to 95° C.).

The order and/or combination of certain steps of the method can be varied. In some embodiments, the devices or methods are capable of performing certain steps in any order or combination. For example, in some embodiments, the residual material and the degraded proteins are flushed in separate or concurrent steps. That is, the residual material is flushed, followed by degradation of residual proteins, followed by flushing degraded proteins from the nucleic acid. In some embodiments, one first degrades the residual proteins, and then flush both the residual material and degraded proteins from the nucleic acid in a combined step.

In some embodiments, the nucleic acid are retained in the device and optionally used in further procedures such as PCR or other procedures manipulating or amplifying nucleic acid. In some embodiments, the devices and systems are capable of performing PCR or other optional procedures. In other embodiments, the nucleic acids are collected and/or eluted from the device. In some embodiments, the devices and systems are capable of allowing collection and/or elution of nucleic acid from the device or system. In some embodiments, the isolated nucleic acid is collected by (i) turning off the second dielectrophoretic field region; and (ii) eluting the nucleic acid from the array in an eluant. Exemplary eluants include water, TE, TBE and L-Histidine buffer.

Nucleic Acids and Yields Thereof

In some embodiments, the method, device, or system described herein is optionally utilized to obtain, isolate, or separate any desired nucleic acid that may be obtained from such a method, device or system. Nucleic acids isolated by the methods, devices and systems described herein include DNA (deoxyribonucleic acid), RNA (ribonucleic acid), and combinations thereof. In some embodiments, the nucleic acid is isolated in a form suitable for sequencing or further manipulation of the nucleic acid, including amplification, ligation or cloning.

In various embodiments, an isolated or separated nucleic acid is a composition comprising nucleic acid that is free from at least 99% by mass of other materials, free from at least 99% by mass of residual cellular material (e.g., from lysed cells from which the nucleic acid is obtained), free from at least 98% by mass of other materials, free from at least 98% by mass of residual cellular material, free from at least 95% by mass of other materials, free from at least 95% by mass of residual cellular material, free from at least 90% by mass of other materials, free from at least 90% by mass of residual cellular material, free from at least 80% by mass of other materials, free from at least 80% by mass of residual cellular material, free from at least 70% by mass of other materials, free from at least 70% by mass of residual cellular material, free from at least 60% by mass of other materials, free from at least 60% by mass of residual cellular material, free from at least 50% by mass of other materials, free from at least 50% by mass of residual cellular material, free from at least 30% by mass of other materials, free from at least 30% by mass of residual cellular material, free from at least 10% by mass of other materials, free from at least 10% by mass of residual cellular material, free from at least 5% by mass of other materials, or free from at least 5% by mass of residual cellular material.

In various embodiments, the nucleic acid has any suitable purity. For example, if a DNA sequencing procedure can work with nucleic acid samples having about 20% residual cellular material, then isolation of the nucleic acid to 80% is suitable. In some embodiments, the isolated nucleic acid comprises less than about 80%, less than about 70%, less than about 60%, less than about 50%, less than about 40%, less than about 30%, less than about 20%, less than about 10%, less than about 5%, or less than about 2% non-nucleic acid cellular material and/or protein by mass. In some embodiments, the isolated nucleic acid comprises greater than about 99%, greater than about 98%, greater than about 95%, greater than about 90%, greater than about 80%, greater than about 70%, greater than about 60%, greater than about 50%, greater than about 40%, greater than about 30%, greater than about 20%, or greater than about 10% nucleic acid by mass.

The nucleic acids are isolated in any suitable form including unmodified, derivatized, fragmented, non-fragmented, and the like. In some embodiments, the nucleic acid is collected in a form suitable for sequencing. In some embodiments, the nucleic acid is collected in a fragmented form suitable for shotgun-sequencing, amplification or other manipulation. The nucleic acid may be collected from the device in a solution comprising reagents used in, for example, a DNA sequencing procedure, such as nucleotides as used in sequencing by synthesis methods.

In some embodiments, the methods described herein result in an isolated nucleic acid sample that is approximately representative of the nucleic acid of the starting sample. In some embodiments, the devices and systems described herein are capable of isolating nucleic acid from a sample that is approximately representative of the nucleic acid of the starting sample. That is, the population of nucleic acids collected by the method, or capable of being collected by the device or system, are substantially in proportion to the population of nucleic acids present in the cells in the fluid. In some embodiments, this aspect is advantageous in applications in which the fluid is a complex mixture of many cell types and the practitioner desires a nucleic acid-based procedure for determining the relative populations of the various cell types.

In some embodiments, the nucleic acid isolated using the methods described herein or capable of being isolated by the devices described herein is high-quality and/or suitable for using directly in downstream procedures such as DNA sequencing, nucleic acid amplification, such as PCR, or other nucleic acid manipulation, such as ligation, cloning or further translation or transformation assays. In some embodiments, the collected nucleic acid comprises at most 0.01% protein. In some embodiments, the collected nucleic acid comprises at most 0.5% protein. In some embodiments, the collected nucleic acid comprises at most 0.1% protein. In some embodiments, the collected nucleic acid comprises at most 1% protein. In some embodiments, the collected nucleic acid comprises at most 2% protein. In some embodiments, the collected nucleic acid comprises at most 3% protein. In some embodiments, the collected nucleic acid comprises at most 4% protein. In some embodiments, the collected nucleic acid comprises at most 5% protein.

In some embodiments, the nucleic acid isolated by the methods described herein or capable of being isolated by the devices described herein has a concentration of at least 0.5 ng/mL. In some embodiments, the nucleic acid isolated by the methods described herein or capable of being isolated by the devices described herein has a concentration of at least 1 ng/mL. In some embodiments, the nucleic acid isolated by the methods described herein or capable of being isolated by the devices described herein has a concentration of at least 5 ng/mL. In some embodiments, the nucleic acid isolated by the methods described herein or capable of being isolated by the devices described herein has a concentration of at least 10 ng/ml.

In some embodiments, about 50 pico-grams of nucleic acid is isolated from about 5,000 cells using the methods, systems or devices described herein. In some embodiments, the methods, systems or devices described herein yield at least 10 pico-grams of nucleic acid from about 5,000 cells. In some embodiments, the methods, systems or devices described herein yield at least 20 pico-grams of nucleic acid from about 5,000 cells. In some embodiments, the methods, systems or devices described herein yield at least 50 pico-grams of nucleic acid from about 5,000 cells. In some embodiments, the methods, systems or devices described herein yield at least 75 pico-grams of nucleic acid from about 5,000 cells. In some embodiments, the methods, systems or devices described herein yield at least 100 pico-grams of nucleic acid from about 5,000 cells. In some embodiments, the methods, systems or devices described herein yield at least 200 pico-grams of nucleic acid from about 5,000 cells. In some embodiments, the methods, systems or devices described herein yield at least 300 pico-grams of nucleic acid from about 5,000 cells. In some embodiments, the methods, systems or devices described herein yield at least 400 pico-grams of nucleic acid from about 5,000 cells. In some embodiments, the methods, systems or devices described herein yield at least 500 pico-grams of nucleic acid from about 5,000 cells. In some embodiments, the methods, systems or devices described herein yield at least 1,000 pico-grams of nucleic acid from about 5,000 cells. In some embodiments, the methods, systems or devices described herein yield at least 10,000 pico-grams of nucleic acid from about 5,000 cells.

Assays and Applications

In some embodiments, the methods described herein further comprise optionally amplifying the isolated nucleic acid by polymerase chain reaction (PCR). In some embodiments, the PCR reaction is performed on or near the array of electrodes or in the device. In some embodiments, the device or system comprise a heater and/or temperature control mechanisms suitable for thermocycling.

PCR is optionally done using traditional thermocycling by placing the reaction chemistry analytes in between two efficient thermoconductive elements (e.g., aluminum or silver) and regulating the reaction temperatures using TECs. Additional designs optionally use infrared heating through optically transparent material like glass or thermo polymers. In some instances, designs use smart polymers or smart glass that comprise conductive wiring networked through the substrate. This conductive wiring enables rapid thermal conductivity of the materials and (by applying appropriate DC voltage) provides the required temperature changes and gradients to sustain efficient PCR reactions. In certain instances, heating is applied using resistive chip heaters and other resistive elements that will change temperature rapidly and proportionally to the amount of current passing through them.

In some embodiments, used in conjunction with traditional fluorometry (ccd, pmt, other optical detector, and optical filters), fold amplification is monitored in real-time or on a timed interval. In certain instances, quantification of final fold amplification is reported via optical detection converted to AFU (arbitrary fluorescence units correlated to analyze doubling) or translated to electrical signal via impedance measurement or other electrochemical sensing.

Given the small size of the micro electrode array, these elements are optionally added around the micro electrode array and the PCR reaction will be performed in the main sample processing chamber (over the DEP array) or the analytes to be amplified are optionally transported via fluidics to another chamber within the fluidic cartridge to enable on-cartridge Lab-On-Chip processing.

In some instances, light delivery schemes are utilized to provide the optical excitation and/or emission and/or detection of fold amplification. In certain embodiments, this includes using the flow cell materials (thermal polymers like acrylic (PMMA) cyclic olefin polymer (COP), cyclic olefin co-polymer, (COC), etc.) as optical wave guides to remove the need to use external components. In addition, in some instances light sources—light emitting diodes—LEDs, vertical-cavity surface-emitting lasers—VCSELs, and other lighting schemes are integrated directly inside the flow cell or built directly onto the micro electrode array surface to have internally controlled and powered light sources. Miniature PMTs, CCDs, or CMOS detectors can also be built into the flow cell. This minimization and miniaturization enables compact devices capable of rapid signal delivery and detection while reducing the footprint of similar traditional devices (i.e. a standard bench top PCR/QPCR/Fluorometer).

Amplification on Chip

In some instances, silicon microelectrode arrays can withstand thermal cycling necessary for PCR. In some applications, on-chip PCR is advantageous because small amounts of target nucleic acids can be lost during transfer steps. In certain embodiments of devices, systems or processes described herein, any one or more of multiple PCR techniques are optionally used, such techniques optionally including any one or more of the following: thermal cycling in the flowcell directly; moving the material through microchannels with different temperature zones; and moving volume into a PCR tube that can be amplified on system or transferred to a PCR machine. In some instances, droplet PCR is performed if the outlet contains a T-junction that contains an immiscible fluid and interfacial stabilizers (surfactants, etc). In certain embodiments, droplets are thermal cycled in by any suitable method.

In some embodiments, amplification is performed using an isothermal reaction, for example, transcription mediated amplification, nucleic acid sequence-based amplification, signal mediated amplification of RNA technology, strand displacement amplification, rolling circle amplification, loop-mediated isothermal amplification of DNA, isothermal multiple displacement amplification, helicase-dependent amplification, single primer isothermal amplification or circular helicase-dependent amplification.

In various embodiments, amplification is performed in homogenous solution or as heterogeneous system with anchored primer(s). In some embodiments of the latter, the resulting amplicons are directly linked to the surface for higher degree of multiplex. In some embodiments, the amplicon is denatured to render single stranded products on or near the electrodes. Hybridization reactions are then optionally performed to interrogate the genetic information, such as single nucleotide polymorphisms (SNPs), Short Tandem Repeats (STRs), mutations, insertions/deletions, methylation, etc. Methylation is optionally determined by parallel analysis where one DNA sample is bisulfite treated and one is not. Bisulfite depurinates unmodified C becoming a U. Methylated C is unaffected in some instances. In some embodiments, allele specific base extension is used to report the base of interest.

Rather than specific interactions, the surface is optionally modified with nonspecific moieties for capture. For example, surface could be modified with polycations, i.e., polylysine, to capture DNA molecules which can be released by reverse bias (−V). In some embodiments, modifications to the surface are uniform over the surface or patterned specifically for functionalizing the electrodes or non electrode regions. In certain embodiments, this is accomplished with photolithography, electrochemical activation, spotting, and the like.

In some applications, where multiple chip designs are employed, it is advantageous to have a chip sandwich where the two devices are facing each other, separated by a spacer, to form the flow cell. In various embodiments, devices are run sequentially or in parallel. For sequencing and next generation sequencing (NGS), size fragmentation and selection has ramifications on sequencing efficiency and quality. In some embodiments, multiple chip designs are used to narrow the size range of material collected creating a band pass filter. In some instances, current chip geometry (e.g., 80 um diameter electrodes on 200 um center-center pitch (80/200) acts as 500 bp cutoff filter (e.g., using voltage and frequency conditions around 10 Vpp and 10 kHz). In such instances, a nucleic acid of greater than 500 bp is captured, and a nucleic acid of less than 500 bp is not. Alternate electrode diameter and pitch geometries have different cutoff sizes such that a combination of chips should provide a desired fragment size. In some instances, a 40 um diameter electrode on 100 um center-center pitch (40/100) has a lower cutoff threshold, whereas a 160 um diameter electrode on 400 um center-center pitch (160/400) has a higher cutoff threshold relative to the 80/200 geometry, under similar conditions. In various embodiments, geometries on a single chip or multiple chips are combined to select for a specific sized fragments or particles. For example a 600 bp cutoff chip would leave a nucleic acid of less than 600 bp in solution, then that material is optionally recaptured with a 500 bp cutoff chip (which is opposing the 600 bp chip). This leaves a nucleic acid population comprising 500-600 bp in solution. This population is then optionally amplified in the same chamber, a side chamber, or any other configuration. In some embodiments, size selection is accomplished using a single electrode geometry, wherein nucleic acid of >500 bp is isolated on the electrodes, followed by washing, followed by reduction of the ACEK high field strength (change voltage, frequency, conductivity) in order to release nucleic acids of <600 bp, resulting in a supernatant nucleic acid population between 500-600 bp.

In some embodiments, the chip device is oriented vertically with a heater at the bottom edge which creates a temperature gradient column. In certain instances, the bottom is at denaturing temperature, the middle at annealing temperature, the top at extension temperature. In some instances, convection continually drives the process. In some embodiments, provided herein are methods or systems comprising an electrode design that specifically provides for electrothermal flows and acceleration of the process. In some embodiments, such design is optionally on the same device or on a separate device positioned appropriately. In some instances, active or passive cooling at the top, via fins or fans, or the like. provides a steep temperature gradient. In some instances the device or system described herein comprises, or a method described herein uses, temperature sensors on the device or in the reaction chamber monitor temperature and such sensors are optionally used to adjust temperature on a feedback basis. In some instances, such sensors are coupled with materials possessing different thermal transfer properties to create continuous and/or discontinuous gradient profiles.

In some embodiments, the amplification proceeds at a constant temperature (i.e, isothermal amplification).

In some embodiments, the methods disclosed herein further comprise sequencing the nucleic acid isolated as disclosed herein. In some embodiments, the nucleic acid is sequenced by Sanger sequencing or next generation sequencing (NGS). In some embodiments, the next generation sequencing methods include, but are not limited to, pyrosequencing, ion semiconductor sequencing, polony sequencing, sequencing by ligation, DNA nanoball sequencing, sequencing by ligation, or single molecule sequencing.

In some embodiments, the isolated nucleic acids disclosed herein are used in Sanger sequencing. In some embodiments, Sanger sequencing is performed within the same device as the nucleic acid isolation (Lab-on-Chip). Lab-on-Chip workflow for sample prep and Sanger sequencing results would incorporate the following steps: a) sample extraction using ACE chips; b) performing amplification of target sequences on chip; c) capture PCR products by ACE; d) perform cycle sequencing to enrich target strand; e) capture enriched target strands; f) perform Sanger chain termination reactions; perform electrophoretic separation of target sequences by capillary electrophoresis with on chip multi-color fluorescence detection. Washing nucleic acids, adding reagent, and turning off voltage is performed as necessary. Reactions can be performed on a single chip with plurality of capture zones or on separate chips and/or reaction chambers.

In some embodiments, the method disclosed herein further comprise performing a reaction on the nucleic acids (e.g., fragmentation, restriction digestion, ligation of DNA or RNA). In some embodiments, the reaction occurs on or near the array or in a device, as disclosed herein.

Other Assays

The isolated nucleic acids disclosed herein may be further utilized in a variety of assay formats. For instance, devices which are addressed with nucleic acid probes or amplicons may be utilized in dot blot or reverse dot blot analyses, base-stacking single nucleotide polymorphism (SNP) analysis, SNP analysis with electronic stringency, or in STR analysis. In addition, such devices disclosed herein may be utilized in formats for enzymatic nucleic acid modification, or protein-nucleic acid interaction, such as, e.g., gene expression analysis with enzymatic reporting, anchored nucleic acid amplification, or other nucleic acid modifications suitable for solid-phase formats including restriction endonuclease cleavage, endo- or exo-nuclease cleavage, minor groove binding protein assays, terminal transferase reactions, polynucleotide kinase or phosphatase reactions, ligase reactions, topoisomerase reactions, and other nucleic acid binding or modifying protein reactions.

In addition, the devices disclosed herein can be useful in immunoassays. For instance, in some embodiments, locations of the devices can be linked with antigens (e.g., peptides, proteins, carbohydrates, lipids, proteoglycans, glycoproteins, etc.) in order to assay for antibodies in a bodily fluid sample by sandwich assay, competitive assay, or other formats. Alternatively, the locations of the device may be addressed with antibodies, in order to detect antigens in a sample by sandwich assay, competitive assay, or other assay formats. As the isoelectric point of antibodies and proteins can be determined fairly easily by experimentation or pH/charge computations, the electronic addressing and electronic concentration advantages of the devices may be utilized by simply adjusting the pH of the buffer so that the addressed or analyte species will be charged.

In some embodiments, the isolated nucleic acids are useful for use in immunoassay-type arrays or nucleic acid arrays.

Exemplary Comparison

Approximately 100 ng of input *E. coli* genome is necessary for conventional manual methods, (e.g., 50 ng of input DNA is required for Nextera, assuming 50% recovery (Epicentre WaterMaster kit claims recovery about 30-60%) from DNA extraction purification). This is equivalent to about 20 million bacteria. In some embodiments of the present invention, less than 10,000 bacteria input is sufficient (e.g., since the chip is self contained and involves less transfers the efficiency is higher). In some embodiments, this is at least a 100 fold reduction in input, which can be important for applications where sample is limited, such as tumor biopsies.

Table 1 below outlines exemplary steps involved to go from *E. coli* to DNA suitable for sequencing. In some instances, conventional methods require centrifugation, several temperatures, wash steps, and numerous transfer steps which are inefficient. In contrast, as described herein, in some embodiments allows the same steps to be carried out by a device that minimizes the pipette transfers and exposure to large virgin surfaces with varying degrees of nonspecific binding properties. In some instances, the device is temperature controlled to provide appropriate reaction conditions. In some instances, PCR, cycle PCR for sequencing pre-amp or full PCR (endpoint, real time or digital) is accomplished off-device or on-device. Off-device includes not on the device but on the same cartridge assembly, connections via fluidic channels or conduits. Furthermore, in some instances PCR amplification is accomplished in the device flow cell chamber, in a PCR tube that is on the cartridge, or though fluidic channels that possess heat zones for temperature cycling. In some instances, the eluate from the device chamber is combined with side channel(s) primed with non aqueous miscible fluid, e.g., oil, and other droplet stabilizers to perform amplification in droplets. In some embodiments, the temperature cycling mechanics are as described above.

In Table 1, the amount of starting material for the conventional processing was 2-5×10$^7$ *E. Coli* cells in approximately 1 ml of water and the entire amount was concentrated on the filters. Using the chip, as disclosed herein, only 1×10$^4$ *E. Coli* cells in approximately 50 microliters was applied to the flow cell. This was 3 orders of magnitude less starting material.

TABLE 1

Comparison of methods for nucleic acid isolation.

| Conventional | An exemplary embodiment provided herein |
|---|---|
| Epicentre WaterMaster DNA Purification Kit | [ON CHIP] |
| Concentrate *E. coli* bacteria on filters | Capture *E. coli*, 1 MHz, 10 Vpp, 10' |
| Lysis solution | Electro-lyse *E. coli*, 200 V DC, 1 msec pulse |
| Proteinase K treatment, 65 C., 15' | De-energize electrodes |
| RNase treatment, 37 C., 30' | Collection, 10 Vpp, 10 KHz |
| Precipitate protein by centrifuge, 10K × g, 4 C., 10' | De-energize electrodes |

TABLE 1-continued

Comparison of methods for nucleic acid isolation.

| Conventional | An exemplary embodiment provided herein |
|---|---|
| Wash isopropanol | Q protease treatment, 37 C., 10' |
| Precipitate protein by centrifuge, 10K × g, 4 C., 10' | Inactivate 70 C., 10' |
| Rinse pellet with 70 ethanol | Collection, 10 Vpp, 10 KHz |
| Resuspend DNA in TE buffer | Wash with Nextera LMW buffer |
| Remove inhibitors, 2K × g, 2' | |
| Repeat 2X | |
| DNA ready for library prep | |
| Epicentre Nextera DNA Sample Prep (Illumina) | |
| 50 ng input DNA (1e7 *E. coli* equiv.) | |
| Fragment with Transposase, 55 C., 5' | Fragment with Transposase, 55 C., 7' |
| Purify with Zymo spin column, 10K × g, 1' | Elute DNA into microtube |
| Add adapters, cycle PCR, 9 cycles | [OFF CHIP] |
| Purify with Zymo spin column, 10K × g, 1' | Add adapters, cycle PCR, 9 cycles |
| | Purify with Zymo spin column, 10K × g, 1' |
| Sequence | Sequence |

In various embodiments (i.e., depending on the AC electrokinetic parameters), cells or other micron scale particles are concentrated to either the low or high field regions. In some instances, the crossover frequency which determines whether a particle moves into or away from the high field region can be tuned by varying the AC frequency, voltage, medium conductivity, adulterating particle polarizability (such as attachment or binding of materials with different DEP characteristics), or electrode geometry. In some instances, nanoscale particles are limited to concentration in the high field region. In some instances, Brownian motion and other hydrodynamic forces limit ability to concentrate in low field regions.

Definitions and Abbreviations

The articles "a", "an" and "the" are non-limiting. For example, "the method" includes the broadest definition of the meaning of the phrase, which can be more than one method.

"Vp-p" is the peak-to-peak voltage.

"TBE" is a buffer solution containing a mixture of Tris base, boric acid and EDTA.

"TE" is a buffer solution containing a mixture of Tris base and EDTA.

"L-Histidine buffer" is a solution containing L-histidine.

"DEP" is an abbreviation for dielectrophoresis.

EXAMPLES

Example 1

Formation of Hydrogel by Spin-coating (Two Coats)

For a layer of hydrogel, approximately 70 microliters of hydrogel is used to coat a 10×12 mm chip.

A low concentration (≤1% solids by volume) cellulose acetate solution is dissolved into a solvent such as acetone, or an acetone and ethanol mixture and applied to an electrode array chip as disclosed herein. The chip is spun at a low rpm rate (1000-3000). The low rpm rate ensures that the height of the gel is in the range of 500 nm or greater.

The first (bottom) coating of cellulose acetate is dried at room temperature, in a convection oven, or a vacuum oven. Optionally, the second layer of cellulose-acetate spin-coat is added immediately.

The second layer of cellulose acetate comprises a high concentration (≥2%) of cellulose acetate dissolved into a solvent such as acetone, or an acetone and ethanol mixture. After a second layer of cellulose acetate is added, the chip is spun at a high rpm rate (9000-12000). The high rpm rate will ensure the height of the gel is in the range of 300 nm or less.

The chip with two layers of cellulose acetate is then dried at room temperature, in a convection oven, or in a vacuum oven.

Example 2

Formation of Hydrogel with Additives by Spin-coating (Two Coats)

For a layer of hydrogel, approximately 70 microliters of hydrogel is used to coat a 10×12 mm chip.

A low concentration (≤1% solids by volume) cellulose acetate solution is dissolved into a solvent such as acetone, or an acetone and ethanol mixture and applied to an electrode array chip as disclosed herein. The chip is spun at a low rpm rate (1000-3000). The low rpm rate ensures that the height of the gel is in the range of 500 nm or greater.

The first (bottom) coating of cellulose acetate is dried at room temperature, in a convection oven, or a vacuum oven. Optionally, the second layer of cellulose-acetate spin-coat is added immediately.

The second layer of cellulose acetate comprises a high concentration (≥2%) of cellulose acetate dissolved into a solvent such as acetone, or an acetone and ethanol mixture. A low concentration (1-15%) of conductive polymer (PEDOT: PSS or similar) is added into the second cellulose acetate solution. After a second layer of cellulose acetate is added, the chip is spun at a high rpm rate (9000-12000). The high rpm rate will ensure the height of the gel is in the range of 300 nm or less.

The chip with two layers of cellulose acetate is then dried at room temperature, in a convection oven, or in a vacuum oven.

Example 3

Formation of Hydrogel with Additives by Spin-coating (Three Coats)

For a layer of hydrogel, approximately 70 microliters of hydrogel is used to coat a 10×12 mm chip.

A low concentration (≤1% solids by volume) cellulose acetate solution is dissolved into a solvent such as acetone, or an acetone and ethanol mixture and applied to an electrode array chip as disclosed herein. The chip is spun at a high rpm rate (9000-12000). The low rpm rate ensures that the height of the gel is in the range of 300 nm or less.

The first (bottom) coating of cellulose acetate is dried at room temperature, in a convection oven, or a vacuum oven. Optionally, the second layer of cellulose-acetate spin-coat is added immediately.

The second layer of cellulose acetate comprises a high concentration (≥2%) of cellulose acetate dissolved into a solvent such as acetone, or an acetone and ethanol mixture. A low concentration (1-15%) of conductive polymer (PEDOT: PSS or similar) is added into the second cellulose acetate solution. After a second layer of cellulose acetate is added, the chip is spun at a low rpm rate (1000-3000). The low rpm rate will ensure that the height of the gel is in the range of 500 nm or greater.

The second coating of cellulose acetate is dried at room temperature, in a convection oven, or a vacuum oven. Optionally, the third layer of cellulose-acetate spin-coat is added immediately.

The third layer of cellulose acetate comprises a high concentration (≥2%) of cellulose acetate dissolved into a solvent such as Acetone, or an Acetone Ethanol mixture. The chip is spun at a high rpm rate (9000-12000). The low rpm rate ensures that the height of the gel is in the range of 300 nm or less.

The chip with three layers of cellulose acetate is then dried at room temperature, in a convection oven, or in a vacuum oven.

Example 4

Chip Construction

Figure 2:
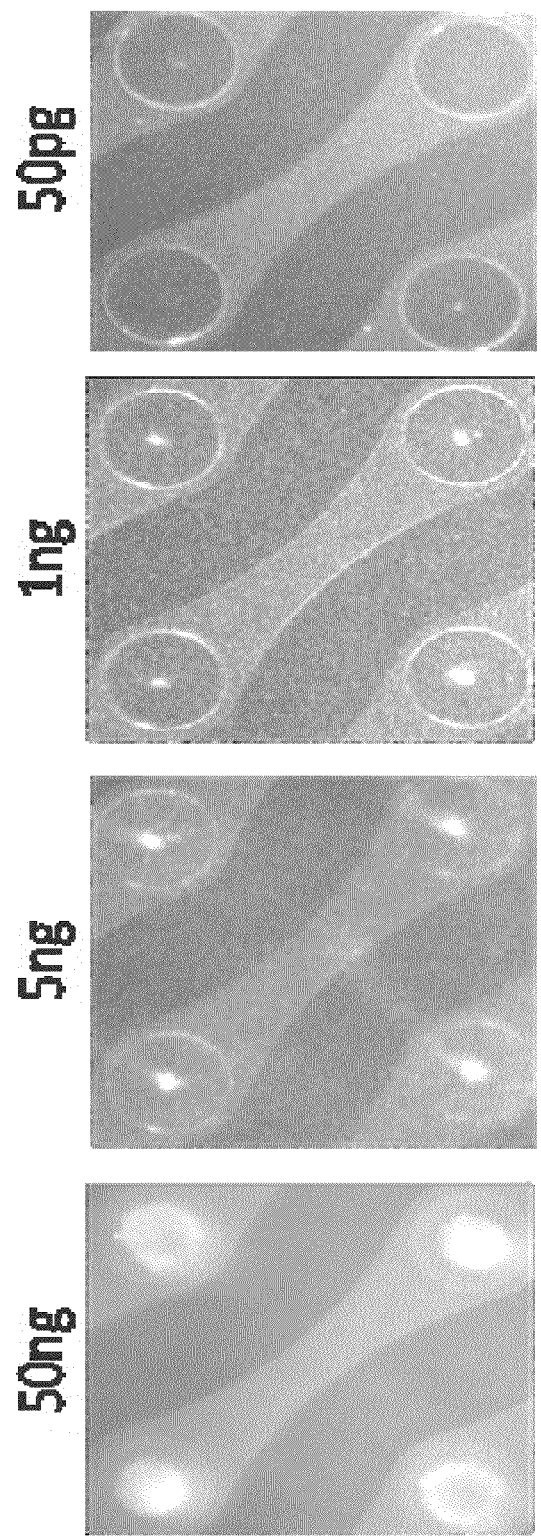
FIG. 2 shows the electrodes associated with various amounts of genomic DNA.
Figure 3:
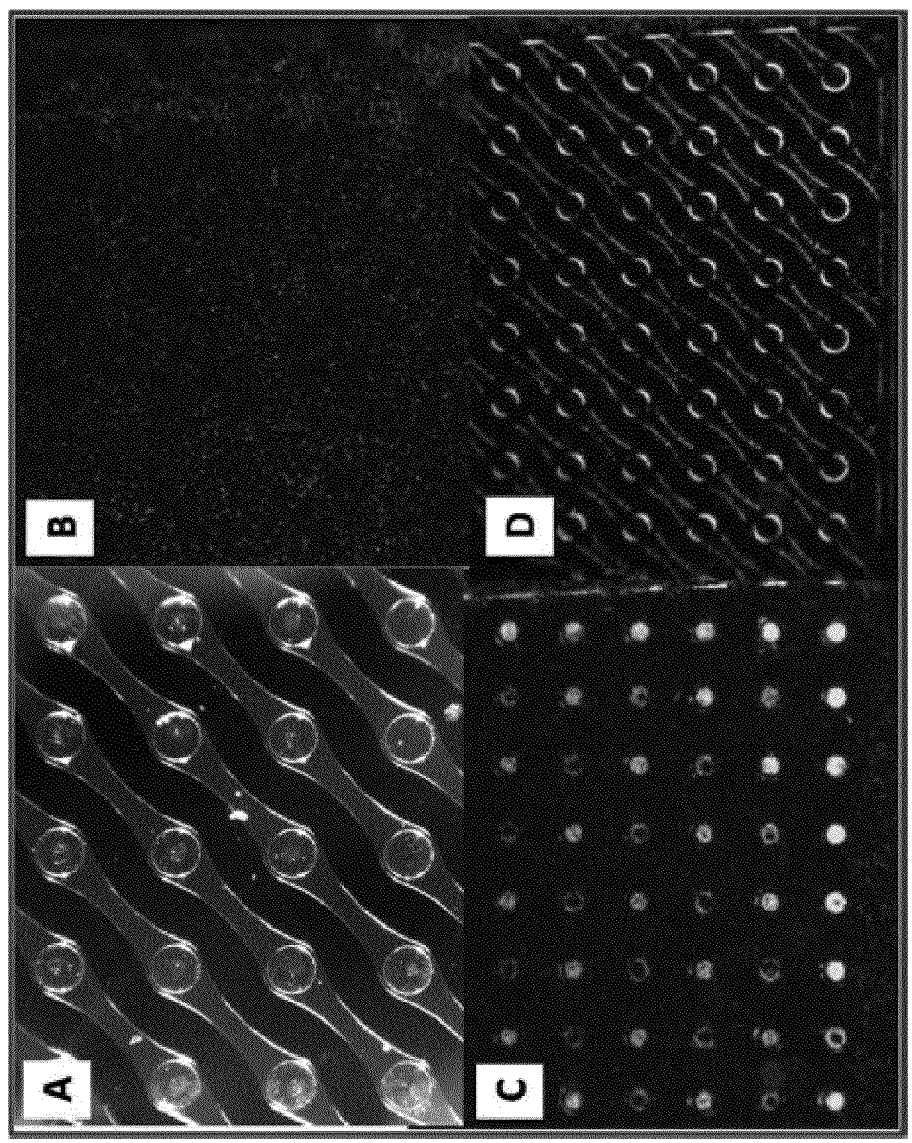
FIG. 3 shows isolation of green fluorescent *E. coli* on an array. (A) shows a bright field view. (B) shows a green fluorescent view of the electrodes before DEP activation. (C) shows *E. coli* on the electrodes after one minute at 10 kHz, 20 Vp-p in 1×TBE buffer. (D) shows *E. coli* on the electrodes after one minute at 1 MHz, 20 Vp-p in 1×TBE buffer.

For FIGS. 2 & 3: A 45×20 custom 80 μm diameter circular platinum microelectrode array on 200 um center-center pitch was fabricated based upon previous results (see references 1-3, below). All 900 microelectrodes are activated together and AC biased to form a checkerboard field geometry. The positive DEP regions occur directly over microelectrodes, and negative low field regions occur between microelectrodes. The array is over-coated with a 200 nm-500 nm thick porous poly-Hema hydrogel layer (Procedure: 12% pHema in ethanol stock solution, purchased from PolySciences Inc., that is diluted to 5% using ethanol. 70 uL of the 5% solution is spun on the above mentioned chip at a 6K RPM spin speed using a spin coater. The chip+hydrogel layer is then put in a 60° C. oven for 45 minutes) and enclosed in a microfluidic cartridge, forming a 50 μL sample chamber covered with an acrylic window (FIG. 1). Electrical connections to microelectrodes are accessed from Molex connectors from the PCB board in the flow cell. A function generator (HP 3245A) provided sinusoidal electrical signal at 10 KHz and 10-14V peak-peak, depending on solution conductivity. Images were captured with a fluorescent microscope (Leica) and an EGFP cube (485 nm emission and 525 nm excitation bandpass filters). The excitation source was a PhotoFluor II 200 W Hg arc lamp.

[1] R. Krishnan, B. D. Sullivan, R. L. Mifflin, S. C. Esener, and M. J. Heller, "Alternating current electrokinetic separation and detection of DNA nanoparticles in high-conductance solutions." Electrophoresis, vol. 29, pages 1765-1774, 2008.
[2] R. Krishnan and M. J. Heller, "An AC electrokinetic method for enhanced detection of DNA nanoparticles." J. Biophotonics, vol. 2, pages 253-261, 2009.
[3] R. Krishnan, D. A. Dehlinger, G. J. Gemmen, R. L. Mifflin, S. C. Esener, and M. J. Heller, "Interaction of nanoparticles at the DEP microelectrode interface under high conductance conditions" Electrochem. Comm., vol. 11, pages 1661-1666, 2009.

Example 5

Isolation of Human Genomic DNA

Human Genomic DNA (gDNA) was purchased from Promega (Promega, Madison, Wis.) and was sized to 20-40 kbp. (Sizing gel not shown.) The gDNA was diluted in DI water to the following concentrations: 50 nanograms, 5 nanograms, 1 nanogram, and 50 picograms. The gDNA was stained using 1×SYBR Green I green fluorescent double stranded DNA dye purchased from Invitrogen (Life Technologies, Carlsbad, Calif.). This mixture was then inserted into the microelectrode arrays and run at 14 Volts peak to peak (Vp-p), at 10 kHz sine wave for 1 minute. At the conclusion of 1 minute, a picture of the microelectrode pads was taken using a CCD camera with a 10× objective on a microscope using green fluorescence filters (FITC) so that the gDNA could be visualized (FIG. 2) The chip was able to identify down to 50 pg of gDNA in 50 µL water, i.e. 1 ng/mL concentration. Additionally, at 50 picograms, each microelectrode had on average ~60 femtograms of DNA since there are 900 microelectrodes on the array. The low-level concentration ability of the ACE device is well within the range of 1-10 ng/mL needed to identify Cfc-DNA biomarkers in plasma and serum (see references 4-6 below).

[4] T. L. Wu et al, "Cell-free DNA: measurement in various carcinomas and establishment of normal reference range." Clin Chim Acta., vol. 21, pages 77-87, 2002.

[5] R. E. Board et al, "DNA Methylation in Circulating Tumour DNA as a Biomarker for Cancer", Biomarker Insights, vol. 2, pages 307-319, 2007.

[6] O. Gautschi et al, "Circulating deoxyribonucleic Acid as prognostic marker in non-small-cell lung cancer patients undergoing chemotherapy." J Clin Oncol., vol. 22, pages 4157-4164, 2004.

Example 6

Isolation of DNA from *E. Coli*

Using the Chip and methods described in Examples 4 and 5, approximately 5000 green fluorescent *E. coli* cells in 50 uL of fluid was inserted into a chip and run using protocol described in caption for FIG. 3. Panel (A) shows a bright field view. Panel (B) shows a green fluorescent view of the electrodes before DEP activation. Panel (C) shows *E. coli* on the electrodes after one minute at 10 kHz, 20 Vp-p in 1×TBE buffer. Panel (D) shows *E. coli* on the electrodes after one minute at 1 MHz, 20 Vp-p in 1×TBE buffer.

Figure 4:
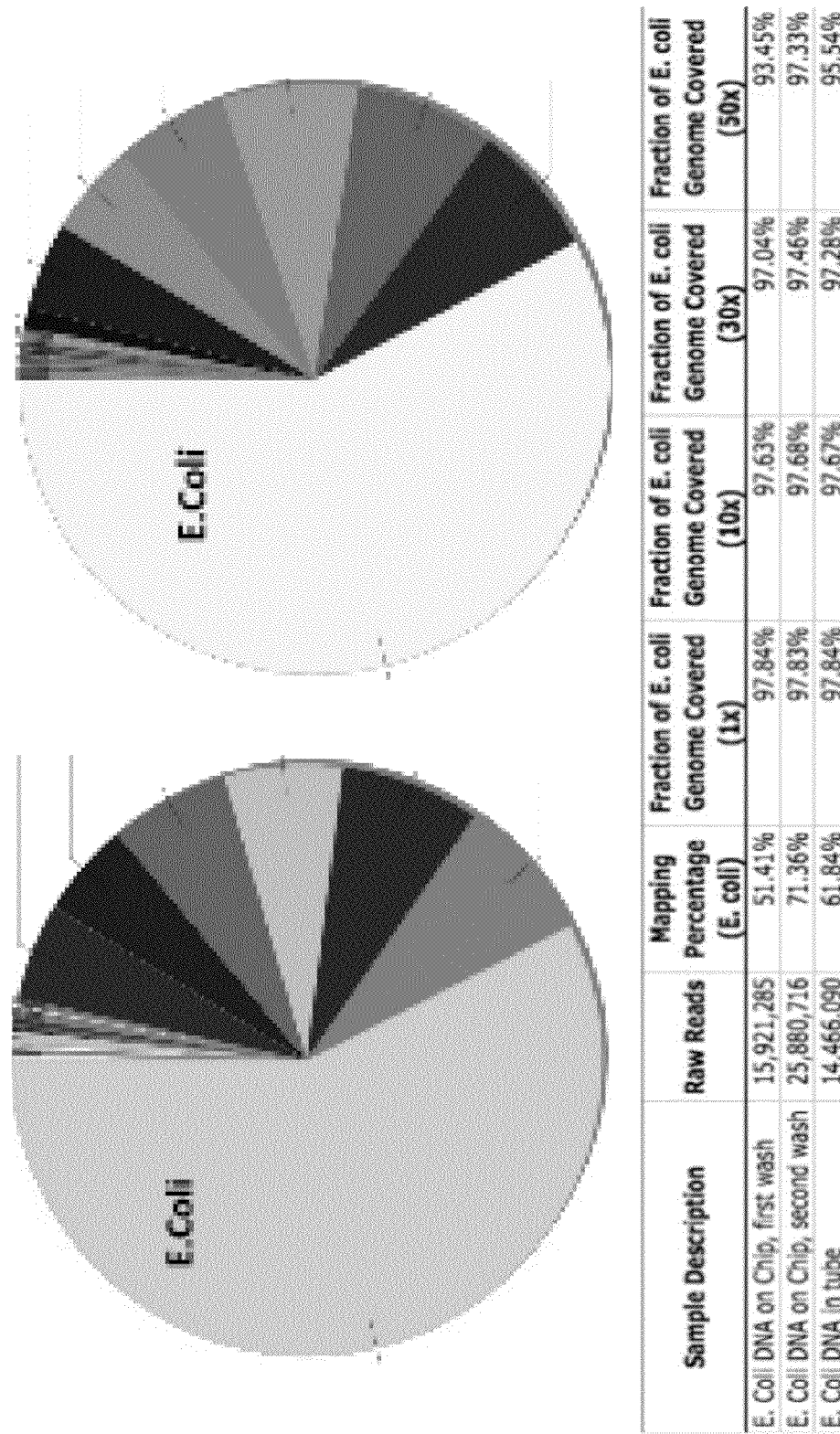
FIG. 4 shows a comparison between the methods of the present invention (top right panel) and the Epicentre™ Water-Master™ DNA purification procedure (top left panel). The pie charts are the distribution of 10,000 Illumina™ sequencing reads BLAST searched against the MEGAN™ database. As shown, a similar percentage of sequencing reads originated from *E. coli* sequence for both methods. The table in the lower panel shows Sequencing coverage and quality of *E. Coli* run through the chip and compared to a control run outside the chip according to manufacturer's protocol.

The *E. coli* depicted in FIG. 3 were lysed using a 100 milli-second 100V DC pulse using the HP 3245A function generator. The lysed particulates were then gathered on the electrode surface using 10 kHz, 10 Vp-p and the Illumina Nextera Protocol was used for library prep for sequencing while the DNA was on the chip (by inserting the appropriate buffers at the appropriate times onto the chip) to tag the DNA for Sequencing. The DNA was then eluted in 50 uL of 1×TBE Buffer and then PCR amplified for 9-12 cycles (using the Nextera Protocol) on a Bio-Rad PCR machine. The amplified DNA was then run on an Illumina GA II Sequencer. DNA from *E. Coli* was also isolated from 1×TBE buffer (10 million cells) using the Epicentre™ WaterMaster™ DNA purification procedure, to serve as a gold standard for comparison. The results are depicted in FIG. 4.

Example 7

Formation of Hydrogel with GVD

Figure 10:
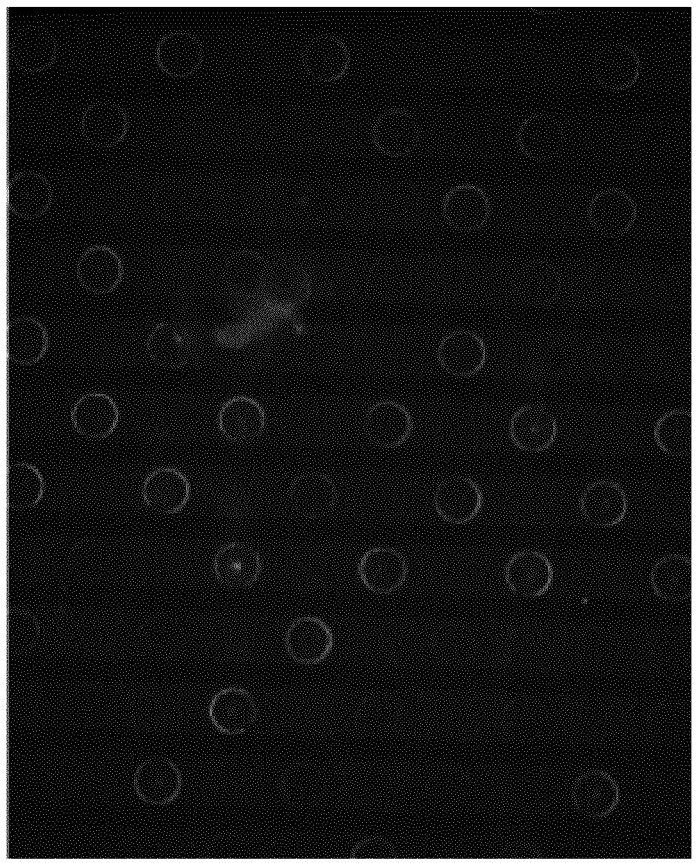
FIG. 10 exemplifies DNA capture on an electrode with a vapor deposited hydrogel layer. Vapor phase coatings of activated monomers form uniform thin film coatings on a variety of substrates. Hydrogels such as pHEMA were deposited in various thickness (100, 200, 300, 400 nm) and crosslinking (5, 25, 40%) density on electrode chips by GVD Corporation (Cambridge, Mass.). The hydrogel films were tested using a standard ACE protocol (no pretreatment, 7 Vp-p, 10 KHz, 2 minutes, 0.5×PBS, 500 ng/ml gDNA labeled with Sybr Green 1). Fluorescence on the electrodes was captured by imaging. The 100 nm thickness, 5% crosslink gel device was found to have strong DNA capture. Optionally, the process could be optimized by changing the deposition rate or anchoring growth to the surface of the microelectrode array (i.e., to the passivation layer and exposed electrodes), using an adhesion promote such as a silane derivative.

Hydrogel, such as polyhydroxyethylmethacrylate (pHEMA) may also be layered onto the chip surface via vapor deposition using proprietary assays developed by GVD Corporation (Cambridge, Mass.) (see www.gvdcorp.com). Hydrogels such as pHEMA were deposited in various thickness (100, 200, 300, 400 nm) and crosslinking (5, 25, 40%) density on electrode chips was performed using technology developed by GVD Corporation. The hydrogel films were tested using a standard ACE protocol (no pretreatment, 7 Vp-p, 10 KHz, 2 minutes, 0.5×PBS, 500 ng/ml gDNA labeled with Sybr Green 1). Fluorescence on the electrodes was captured by imaging. FIG. 10 shows that 100 nm thickness, 5% crosslink gel device was found to have strong DNA capture. The process could also be optimized by changing the deposition rate or anchoring growth to the surface of the microelectrode array (i.e., to the passivation layer and exposed electrodes), using an adhesion promoter such as a silane derivative.

Example 8

Performance of Disclosed Device and Method v. Conventional Method

QIAGEN® circulating nucleic acid Purification kit (cat #55114) was used to purify 1 ml of plasma from chronic lymphocytic leukemia (CLL) patients, according to manufacturer's protocol. Briefly, incubation of 1 ml plasma with Proteinase K solution was performed for 30 minutes at 60° C. The reaction was quenched on ice and the entire volume was applied to a QIAamp Mini column connected to a vacuum. The liquid was pulled through the column and washed with 3 different buffers (600-750 ul each). The column was centrifuged at 20,000×g, 3 minutes and baked at 56° C. for 10 minutes to remove excess liquid. The sample was eluted in 55 µl of elution buffer with 20,000×g, 1 minute centrifugation. Total processing time was ~2.5 hours.

The chip die size was 10×12 mm, with 60-80 µm diameter Pt electrodes on 180-200 µm center-to-center pitch, respectively. The array was overcoated with a 5% pHEMA hydrogel layer (spun cast 6000 rpm from Ethanol solution, 12% pHEMA stock from Polysciences). The chip was pretreated using 0.5×PBS, 2V rms, 5 Hz, 15 seconds. The buffer was removed and 25 µl of CLL patient plasma was added. DNA was isolated for 3 minutes at 11 V p-p, 10 Khz, then washed with 500 µl of TE buffer at a 100 µl/min flow rate, with power ON. The voltage was turned off and the flow cell volume was eluted into a microcentrifuge tube. Total processing time was ~10 minutes.

The same process can be applied to fresh whole blood without modification. Ability to extract and purify DNA from whole undiluted blood is uniquely enabled by the chip technology disclosed herein.

DNA quantitation was performed on the Qiagen and chip elutes using PicoGreen according to manufacturer's protocol (Life Tech) (Table 2).

Subsequent gel electrophoresis, PCR and Sanger sequencing reactions showed similar performance for both extraction techniques with the chip being able to process whole blood as well as plasma. Mann-Whitney U non-parametric statistical test was also run between DNA amounts isolated from plasma using the Qiagen and chip techniques. There was no statistical difference (p<0.05 two-tailed) using either method of DNA purification.

TABLE 2

DNA purification, chip v. Qiagen
Values are in ng/ml and normalized to original
plasma sample volume for comparison purposes.

| Patient | Chip - plasma | Qiagen - plasma | Chip - blood |
|---|---|---|---|
| normal A | 139 | 39 | 274 |
| normal B | 206 | 80 | 114 |
| normal C | 133 | 32 | 97 |
| TJK 528 | 320 | 547 | 167 |
| TJK 851 | 218 | 393 | 307 |

TABLE 2-continued

DNA purification, chip v. Qiagen
Values are in ng/ml and normalized to original
plasma sample volume for comparison purposes.

| Patient | Chip - plasma | Qiagen - plasma | Chip - blood |
|---|---|---|---|
| TJK 1044 | 285 | 424 | 794 |
| TJK 334 | 261 | 1387 | 666 |
| TJK 613 | 179 | 53 | 257 |
| TJK 762 | 145 | 367 | 314 |
| TJK 847 | 886 | 1432 | 811 |
| TJK 248 | 84 | 119 | 448 |
| TJK 1024 | 302 | 169 | 332 |
| TJK 1206 | 584 | 396 | 1435 |
| TJK 1217 | 496 | 146 | 584 |
| TJK 1262 | 87 | 84 | 1592 |
| TJK 1311 | 119 | 257 | 1825 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for isolating a nucleic acid from a fluid, the method comprising:
   a. applying the fluid to a device, the device comprising an array of electrodes capable of establishing an AC electrokinetic field region;
   b. concentrating cells and/or other particulate material in the fluid in a first AC electrokinetic field region, wherein the conductivity of the fluid is greater than 300 mS/m;
   c. isolating nucleic acid in a second AC electrokinetic field region, wherein the second AC electrokinetic field is a dielectrophoretic high field region; and
   d. flushing the concentrated cells and/or other particulate material from the first AC electrokinetic field region.

2. The method of claim 1, wherein the AC electrokinetic field is produced using an alternating current having a voltage of 1 volt to 40 volts peak-peak, and/or a frequency of 5 Hz to 5,000,000 Hz and duty cycles from 5% to 50%.

3. The method of claim 1, wherein the conductivity of the fluid is greater than 500 mS/m.

4. The method of claim 1, wherein the electrodes are selectively energized to provide the first dielectrophoretic field region, wherein the first dielectrophoretic field region is a low field region, and subsequently or continuously selectively energized to provide the second dielectrophoretic field region.

5. The method of claim 1, wherein the array of electrodes is spin-coated with a hydrogel having a thickness between about 0.1 microns and 1 micron.

6. The method of claim 5, wherein the hydrogel comprises two or more layers of a synthetic polymer.

7. The method of claim 5, wherein the hydrogel has a viscosity between about 0.5 cP to about 5 cP prior to spin-coating.

8. The method of claim 5, wherein the hydrogel has a conductivity between about 0.1 S/m to about 1.0 S/m.

9. The method of claim 1, wherein the isolated nucleic acid comprises less than about 10% non-nucleic acid cellular material or cellular protein by mass.

10. The method of claim 1, wherein the method is completed in less than 10 minutes.

11. The method of claim 1, wherein the array of electrodes comprises a wavy line configuration, wherein the configuration comprises a repeating unit comprising the shape of a pair of dots connected by linker, wherein the linker tapers inward toward the midpoint between the pair of dots, wherein the diameters of the dots are the widest points along the length of the repeating unit, wherein the edge to edge distance between a parallel set of repeating units is equidistant, or roughly equidistant.

12. The method of claim 1, wherein the array of electrodes comprises a passivation layer with a relative electrical permittivity from about 2.0 to about 4.0.

13. The method of claim 1, wherein the fluid is a bodily fluid, an environmental sample, food or beverage, growth medium or water.

14. A method for isolating a nucleic acid from a fluid, the method comprising:
   a. applying the fluid to a device, the device comprising an array of electrodes capable of establishing an AC electrokinetic field region;
   b. concentrating cells and/or other particulate material in the fluid in a first AC electrokinetic field region, wherein the conductivity of the fluid is greater than 300 mS/m;
   c. isolating nucleic acid in a second AC electrokinetic field region, wherein the second AC electrokinetic field is a dielectrophoretic high field region;
   d. flushing the concentrated cells and/or other particulate material from the first AC electrokinetic field region;
   e. degrading residual proteins and/or material; and
   f. flushing the degraded residual proteins and/or material from the isolated nucleic acid.

15. The method of claim 14, wherein the residual proteins and/or material are degraded by chemical and/or enzymatic degradation agents.

16. The method of claim 14, wherein the AC electrokinetic field is produced using an alternating current having a voltage of 1 volt to 40 volts peak-peak, and/or a frequency of 5 Hz to 5,000,000 Hz and duty cycles from 5% to 50%.

17. The method of claim 14, wherein the electrodes are selectively energized to provide the first dielectrophoretic field region, wherein the first dielectrophoretic field region is a low field region, and subsequently or continuously selectively energized to provide the second dielectrophoretic field region.

18. The method of claim 14, wherein the array of electrodes is spin-coated with a hydrogel having a thickness between about 0.1 microns and 1 micron.

19. The method of claim 14, wherein the array of electrodes comprises a wavy line configuration, wherein the configuration comprises a repeating unit comprising the shape of a pair of dots connected by linker, wherein the linker tapers inward toward the midpoint between the pair of dots, wherein the diameters of the dots are the widest points along the length of the repeating unit, wherein the edge to edge distance between a parallel set of repeating units is equidistant, or roughly equidistant.

20. The method of claim 14, wherein the array of electrodes comprises a passivation layer with a relative electrical permittivity from about 2.0 to about 4.0.

21. The method of claim 14, wherein the fluid is a bodily fluid, an environmental sample, food or beverage, growth medium or water.

\* \* \* \* \*